(12) United States Patent
Nolan et al.

(10) Patent No.: US 11,765,119 B2
(45) Date of Patent: Sep. 19, 2023

(54) SYSTEMS AND METHODS FOR FACILITATING TRIGGER-ASSOCIATED USER MESSAGING

(71) Applicant: KONINKLIJKE PHILIPS N.V., Eindhoven (NL)

(72) Inventors: Julian Charles Nolan, Pully (CH); Melanie Jane Windridge, Amersham (GB); Joyca Petra Wilma Lacroix, Eindhoven (NL); Cees Van Berkel, Hove (GB); Jan Tatousek, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 686 days.

(21) Appl. No.: 16/866,246

(22) Filed: May 4, 2020

(65) Prior Publication Data

US 2020/0267110 A1    Aug. 20, 2020

Related U.S. Application Data

(63) Continuation-in-part of application No. 14/511,317, filed on Oct. 10, 2014, now abandoned.

(51) Int. Cl.
| | |
|---|---|
| H04L 51/226 | (2022.01) |
| G06F 9/54 | (2006.01) |
| G06N 20/00 | (2019.01) |
| G16H 80/00 | (2018.01) |
| G06N 3/084 | (2023.01) |

(52) U.S. Cl.
CPC ............ *H04L 51/226* (2022.05); *G06F 9/546* (2013.01); *G06N 3/084* (2013.01); *G06N 20/00* (2019.01); *G16H 80/00* (2018.01)

(58) Field of Classification Search
CPC ........ G16H 20/10; G16H 20/00; G06N 20/00; H04L 51/226
See application file for complete search history.

(56) References Cited

U.S. PATENT DOCUMENTS

| | | |
|---|---|---|
| 5,390,238 A | 2/1995 | Kirk et al. |
| 6,421,650 B1 | 7/2002 | Goetz et al. |
| 6,717,598 B1 | 4/2004 | Melton, Jr. et al. |

(Continued)

FOREIGN PATENT DOCUMENTS

| | | | | |
|---|---|---|---|---|
| GB | 2410850 A | * | 8/2005 | ........... G01S 5/0252 |
| WO | WO-2011163625 A1 | * | 12/2011 | ......... G06F 19/3418 |

*Primary Examiner* — Kamal B Divecha
*Assistant Examiner* — Sandarva Khanal

(57) ABSTRACT

In certain embodiments, trigger-associated user messaging may be facilitated. In some embodiments, a first set of candidate users for messaging with a first user in connection with occurrence of a first trigger associated with the first user may be obtained. The first user may be monitored via one or more sensors for occurrence of the first trigger. A first occurrence of the first trigger may be determined based on the monitoring. Based on the first occurrence of the first trigger, the first set of candidate users may be accessed to initiate messaging between the first user and one or more users of the first set of candidate users. Messaging between the first user and a second user (of the first set of candidate users) may be initiated based on the second user having a higher priority than a third user of the first set of candidate users.

17 Claims, 9 Drawing Sheets

(56) References Cited

U.S. PATENT DOCUMENTS

| | | | |
|---|---|---|---|
| 6,728,341 B1 | 4/2004 | Puchek et al. | |
| 6,985,869 B1 | 1/2006 | Stoll et al. | |
| 7,519,165 B1* | 4/2009 | Rodkey | H04M 3/50 |
| | | | 379/252 |
| 9,235,547 B1* | 1/2016 | Hartman, II | H04L 51/226 |
| 9,679,259 B1* | 6/2017 | Frind | G06N 20/00 |
| 10,540,607 B1* | 1/2020 | Oldridge | G06N 20/00 |
| 2007/0182628 A1* | 8/2007 | Pomerantz | G01S 19/06 |
| | | | 342/357.43 |
| 2007/0288932 A1 | 12/2007 | Horvitz | G06Q 10/107 |
| | | | 719/313 |
| 2008/0103371 A1* | 5/2008 | Rosenblum | G16H 20/30 |
| | | | 600/300 |
| 2009/0307345 A1 | 12/2009 | Carter | G06Q 30/02 |
| | | | 709/224 |
| 2011/0125555 A1 | 5/2011 | Fradkin | G06Q 10/06395 |
| | | | 705/7.41 |
| 2011/0131060 A1 | 6/2011 | Schuster | G06Q 10/10 |
| | | | 705/3 |
| 2012/0066140 A1 | 3/2012 | Hegeman | G06Q 10/10 |
| | | | 705/319 |
| 2012/0179002 A1 | 7/2012 | Brunetti et al. | |
| 2012/0210240 A1 | 8/2012 | Neystadt | G06Q 30/0282 |
| 2012/0252401 A1* | 10/2012 | Rothschild | G08B 25/005 |
| | | | 455/404.1 |
| 2012/0254184 A1 | 10/2012 | Choudhary et al. | |
| 2013/0138663 A1 | 5/2013 | Shivashankar et al. | |
| 2014/0088995 A1* | 3/2014 | Damani | G16H 20/10 |
| | | | 705/2 |
| 2014/0351374 A1* | 11/2014 | Canoy | H04L 67/10 |
| | | | 709/217 |
| 2019/0074080 A1* | 3/2019 | Appelbaum | H04L 51/02 |
| 2021/0334589 A1* | 10/2021 | Plant | G06F 9/542 |
| 2022/0068453 A1* | 3/2022 | Simpson | G16H 10/20 |

* cited by examiner

SYSTEMS AND METHODS FOR FACILITATING TRIGGER-ASSOCIATED USER MESSAGING

RELATED APPLICATION(S)

This application is a continuation-in-part of U.S. patent application Ser. No. 14/511,317, filed Oct. 10, 2014, which is hereby incorporated by reference herein in its entirety.

FIELD OF THE INVENTION

The present invention relates to systems and methods for facilitating trigger-associated user messaging.

BACKGROUND

There are many illnesses that require long term management. For example, a patient with a long term health condition may have a therapeutic regime prescribed by a doctor, that the patient should then adhere to. The therapeutic regime may manage the patient's symptoms, and the objective of the therapeutic regime is to manage the patient's condition and to help to achieve a positive clinical outcome. It will be appreciated that non-adherence with the therapeutic regime may cause the patient's health to deteriorate.

Alternatively, a patient with a long term health condition may require a therapeutic regime that depends on the symptoms. For such patients, it may be necessary to monitor the patient's symptoms, taking appropriate medical action if the patient's symptoms worsen.

An example of a chronic disease cycle is provided in FIG. 1. Such a pattern is common to many long term health conditions. For a patient with such a chronic condition, assuming that an outright cure is not possible, stability S1 represents the most positive outcome for the patient. When the patient is stable, the patient's symptoms may fluctuate from day to day, but there is no downward trend. Maintaining stability is likely to be the goal of a therapeutic regime aimed at managing a long term health condition.

If the patient's condition worsens (see path P1), there may be an event onset S2. The term "event onset" refers to a moment when the patient becomes unstable, but not yet acute (that is the next state on the circle). The event could be triggered by the patient contracting another illness (e.g. a cold) or by some other cause that worsens the patient's condition. The event might typically be the first signs of the patient's worsening condition manifesting themselves. The event refers here to the unstable state, which requires some intervention to bring the patient back into a stable state. Such intervention can be change of the patient's medication, ambulatory intervention of the physician or in the worst case hospitalization.

After the event onset S2, if the patient's condition is properly managed (e.g. a corrective action is taken), then the patient's condition may improve and the patient might go back to the stability phase S1, via path P2. However, if the patient's condition is not properly managed and/or the patient's symptoms worsen, then the patient may need to be admitted to hospital S3 via path P3. In general terms, the aim of an admission to hospital S3 is to discharge the patient S4 (via path P4) as soon as possible (i.e. to minimize inpatient treatment). After that recovery continues in the recovery step S5 (via path P5), with the aim of the patient becoming stable again (via path P6). Hence, it is desirable to identify the event soon after its onset, because it is likely that as more time that passes, more expensive interventions will have to be used to bring the patient back to the stable state.

Hence, the patient's long term health condition can be visualized in terms of two loops. The first loop involves stability S1 moving to onset S2, and then back to stability S1. This first loop represents an ideal management of an event of instability for a patient with a long term health condition. The second loop involves admission S3, discharge S4 and recovery S5 after the onset. In terms of the drain on resources on a health care system, typically the costs associated with admitting a patient to hospital dwarf the costs associated with maintaining stability.

It is known to provide devices for messaging. For examples, there are web forums in which users can post messages of support for each other. This might be in the form of a user starting a forum thread in which other users can post replies. Such systems present a potentially large number of messages (e.g. replies to a forum thread) to the user, with the messages presented in date order. Hence, with such systems important messages can be missed. Likewise conventional messaging systems such as email or SMS messages typically present the user with received messages in date order, and again important messages can be missed.

SUMMARY

Certain embodiments described herein relate to methods, apparatuses, and/or systems for facilitating trigger-associated user messaging, including, for example, increasing the likely impact of user messaging as described herein.

In some embodiments, training user datasets representing a plurality of users may be obtained. Individual user dataset of the training user datasets may comprise data representing one or more attributes of a user of the plurality of users. The training user datasets may be provided to a neural network to train the neural network in a first stage to predict a set of candidate users (e.g., a list of candidate users for messaging with a user in connection with occurrence of a trigger associated with the user). Training response data may be provided to the neural network as reference feedback to train the neural network in a second stage. The neural network may update one or more layers of the neural network (e.g., one or more weights, biases, or other parameters of the neural network layers) based on the training response data. The training response data may comprise data related to responses of the user to messaging with one or more users of the set of candidate users. In this way, for example, the neural network may be trained to more accurately predict one or more sets of candidate users.

In some embodiments, subsequent to the training of the neural network, a first set of candidate users (e.g., a list of candidate users for messaging with a first user in connection with occurrence of a first trigger associated with the first user) may be obtained from the neural network. As an example, the first set of candidate users may comprise a second user, a third user, or other users. The first user may be monitored) for occurrence of the first trigger. In some embodiments, the first user may be monitored for adherence via one or more sensors. For example, the sensors may include one or more of monitor mechanisms (13, 23, 33), one or more physiological sensors, and/or other sensors. Based on the monitoring indicating a first occurrence of the first trigger, the first set of candidate users may be accessed to initiate messaging between the first and one or more users of the first set of candidate users. Messaging between the first user and the second user may be initiated (e.g., based on the second user having a higher priority than the third user of the first set of candidate users). Messaging between the first user and the third user may be initiated based on (i) the third user having a higher priority than one or more other users of the first set of candidate users and (ii) the second user being determined to be unavailable.

Various other aspects, features, and advantages of the invention will be apparent through the detailed description of the invention and the drawings attached hereto. It is also to be understood that both the foregoing general description and the following detailed description are examples and not restrictive of the scope of the invention.

BRIEF DESCRIPTION OF THE DRAWINGS

Embodiments of the invention will now be described, by way of example only, with reference to the accompanying drawings, in which.

DETAILED DESCRIPTION OF THE EMBODIMENTS

Figure 1:
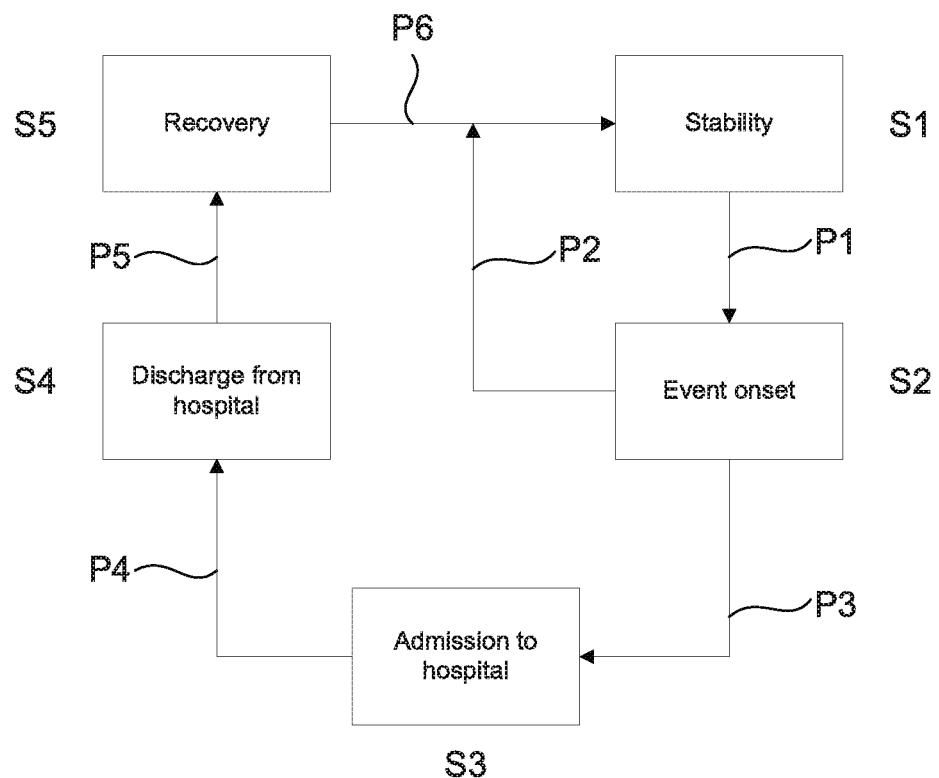
FIG. 1 shows a schematic of a cycle of patient condition and treatment states during the chronic disease.
Figure 2:
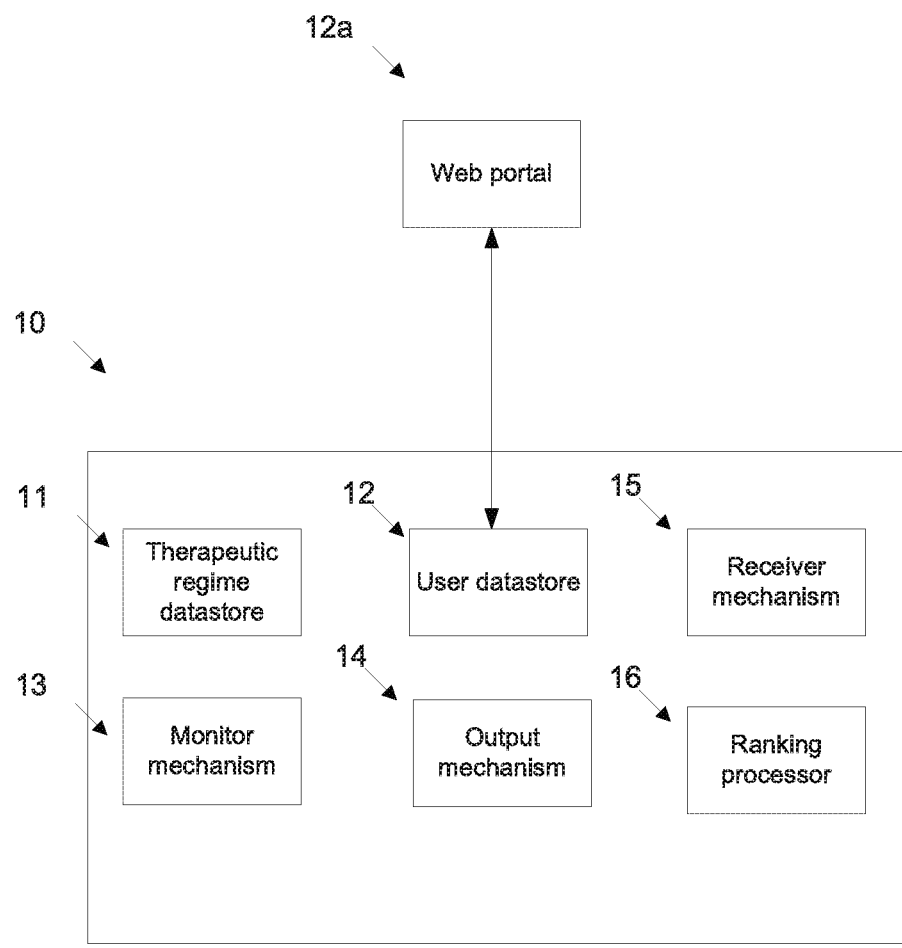
FIG. 2 schematically shows a system for monitoring a user according to one or more embodiments.

FIG. 2 schematically shows a system 10 for messaging a user according to a first embodiment of the invention. In some embodiments, the system 10 could be used by a first user with a long term health condition, with the first user having a therapeutic regime comprising a number of therapeutic activities that the user should perform to adhere to the therapeutic regime.

In some embodiments, system 10 may facilitate obtaining a first set of candidate users for messaging with the first user. In some embodiments, messaging the first user may be based on occurrence of one or more triggers associated with the first user. The triggers may include any failure to adhere to the therapeutic regime. In some embodiments, the triggers may include one or more trigger types. For example, a medication trigger may refer to failure to take a medication, a therapeutic (or non-therapeutic) activity trigger may refer to failure to complete a therapeutic activity and/or a non-therapeutic activity (e.g., a diet, an exercise, watching an informational video, reading specific directions, sleep schedule, and/or other therapeutic and non-therapeutic activities as described herein), a schedule trigger may refer to failure to adhere to a specific schedule, and/or other types of triggers related to other failures to adhere to the therapeutic regime.

In some embodiments, the trigger types may include deviation predictor triggers. For example, a deviation predictor trigger may refer to a prediction that the user might deviate from the therapeutic regime. This may allow for preventing deviation from the regime and act in a preventative manner instead of reactively. In some embodiments, occurrence of a deviation predictor trigger may be based on sensor data from the sensors. For example, occurrence of a deviation predictor may be based on monitoring one or more emotions, and/or behavior (e.g., that might be predictive of deviations from the regime) of the subject. This might indicate a state of mind of the user and his level of interest in various activities, which in turn might predict that that he might adhere or not adhere to the regime. In some embodiments, one or more emotions and/or behavior of the subject may be detected based on the user's facial expressions, demeanor, activities (or lack thereof). In some embodiments, a camera, video feed, an activity sensor, a scale, and/or other sensors (e.g., the sensors described herein) may be used to monitor emotions and/or behavior of the subject. For example, if the first user spends a long time sleeping, this might indicate that he might be experiencing a lack of interest in other activities, which in turn might predict that that he might deviate (or not adhere) to the regime.

In some embodiments, occurrence of a trigger may refer to a time or a time interval the trigger took place. For example, at the time, within minutes, hours, or days of determining that the first user failed to adhere to the therapeutic regime. In some embodiments, system 10 may be configured to determine that a trigger has occurred when a predetermined amount of time has passed since the first user was supposed to perform the activity (e.g., if the user doesn't take his medication within an interval of time). In some embodiments, a trigger may occur if the first user takes his medication (or perform any portion of the therapeutic regime) but not at a consistent scheduled time. In some embodiments, system 10 may be configured to determine one or more types of occurrences based on each type of activity. For example, system 10 may determine that a medication trigger has occurred if the first user does not take a medication within hours, but determines a physical activity trigger if the first user fails to perform a physical exercise for few days.

In some embodiments, occurrence of the triggers may be determined based on monitoring of the first user for occurrence of the triggers. In some embodiments, one or more sensors are configured to monitor adherence of the first user. For example, the sensors may be configured to determine if the first user performs one or more activities related to the therapeutic regime and produce an adherence result for that activity based on the determination. Hence, the sensors may determine if the first user adheres or does not adhere to the therapeutic regime by determining if the activities in the therapeutic regime are performed. In some embodiments, the sensors may be configured to provide monitoring data based on monitoring therapeutic activities, non-therapeutic activities, and other activities related to the first user via one or more monitor mechanisms for therapeutic and non-therapeutic activities (e.g., monitor mechanism 13, 23, 33 described herein in detail below).

In some embodiments, the sensors may include one or more physiological sensors configured to monitor medical conditions of the user physiological data indicating a condition of the user, may be obtained from the physiological sensors. As an example, in some embodiments, the physiological data related to the user may be obtained via a wearable device (e.g., a monitoring device embedded in a body of the user, attached to the user, etc.), via a web interface or mobile application, via one or more databases, etc. In some embodiments, the physiological sensors may include one or more of a heart monitor, an oximeter, a thermometer, a scale, a breathing monitor, a sleep monitor, and/or other physiological sensors. In some embodiments, the physiological sensors may be included and/or in addition to the monitor mechanisms 13, 23, and 33.

In some embodiments, the first set of candidate users may include users having similar attributes (e.g., one or more attributes described herein below) as the first user. The first set of candidate users may include a second user, a third user, and/or any number of users. In some embodiment, responsive to occurrence of the first trigger, system 10 may be configured to access the first set of candidate users to initiate messaging between the first user and the second user based on similarity of attributes between the first user and the second user. In some embodiments, system 10, may be configured to determine a priority for each of the users of the set of candidate users (e.g., ranking second users as described herein). In some embodiments, the priority may be determined based on one or more attributes of the users of the set of candidate users. For example, responsive to occurrence of the first trigger, system 10 may be configured to access the first set of candidate users to initiate messaging between the first user and the second user responsive to the second user having a higher priority than the third user. In some embodiments, the priority of the users may be determined based on a type of trigger, the type of occurrence, and/or priorities.

In some embodiments, system 10 may be configured to provide data (e.g., one or more datasets) representing one or more attributes of the users, one or more trigger types, one or more occurrence types, and/or other data as training datasets to one or more prediction models (e.g., attribute prediction model, trigger prediction model, occurrence prediction model, etc.) to predict a set of candidate users for messaging with the first user. In some embodiments, the prediction models may be updated based on training response data related to responses of the user to messaging with one or more users of the set of candidate users. For example, training response data related to predicted responses of the user to messaging with one or more users may be provided to the prediction models as reference feedback, and the prediction models may update one or more portions of the prediction models based on the predicted responses. In some embodiments, the training response data may include subsequent behavior of the user in line (and/or as a result of) with the message.

In some embodiments, system 10 may be configured to obtain training user datasets representing a plurality of users, each user dataset of the training user datasets comprising data representing one or more attributes of a user of the plurality of users. For example, the attributes of a user of the plurality of users may include personal relationship with the first user (e.g., family member, friend, colleague, social network relationship, etc.). Another attribute may be location proximity (e.g., measured in terms of the distance) between a user of the plurality of users and the first user. Another attribute may be frequency of contact between a user of the plurality of users and the first user. In some embodiments, an attribute of a user may include similarity in health condition, symptoms, care plan, and/or similar therapeutic activities as the first user. In some embodiments, the attributes of a user of the plurality of users may include, frequency of contact, and/or previous or current discussions with the first user (e.g., through a social network, forum, etc.) Another attribute may include previous or current discussions of similar issues with users other than the first user. In some embodiments, the attributes of a user of the plurality of users may include responsiveness of the first user to previous messages from this user. Another attribute may include responsiveness of other users (other than the first user) to message from this user (indicating influence on other users).

In some embodiments, system 10 may provide, in a first stage, the training user datasets to train a prediction model to predict a set of candidate users for messaging with a user in connection with occurrence of a trigger associated with the user. The prediction model may be updated based on training response data comprising data related to responses of the user to messaging with one or more users of the set of candidate users. For example, training response data (e.g., including data related to responses of the user to messaging with one or more users of the set of candidate users) may be provided to the prediction model as reference feedback to train the prediction model in a second stage, and the prediction model may update one or more layers of the prediction model based on the training response data. Subsequent to the training of the prediction model, a first set of candidate users for messaging with a first user may be obtained from the prediction model.

In some embodiments, the prediction model may include one or more neural networks or other machine learning models. As an example, neural networks may be based on a large collection of neural units (or artificial neurons). Neural networks may loosely mimic the manner in which a biological brain works (e.g., via large clusters of biological neurons connected by axons). Each neural unit of a neural network may be connected with many other neural units of the neural network. Such connections can be enforcing or inhibitory in their effect on the activation state of connected neural units. In some embodiments, each individual neural unit may have a summation function which combines the values of all its inputs together. In some embodiments, each connection (or the neural unit itself) may have a threshold function such that the signal must surpass the threshold before it propagates to other neural units. These neural network systems may be self-learning and trained, rather than explicitly programmed, and can perform significantly better in certain areas of problem solving, as compared to traditional computer programs. In some embodiments, neural networks may include multiple layers (e.g., where a signal path traverses from front layers to back layers). In some embodiments, back propagation techniques may be utilized by the neural networks, where forward stimulation is used to reset weights on the "front" neural units. In some embodiments, stimulation and inhibition for neural networks may be more free-flowing, with connections interacting in a more chaotic and complex fashion.

Figure 2A:
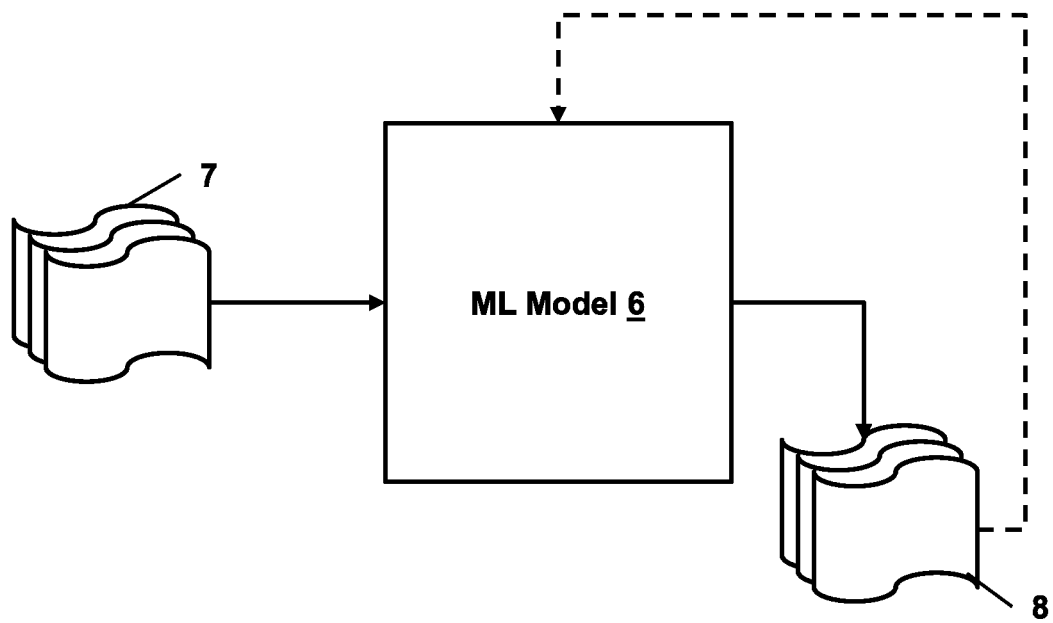
FIG. 2A shows a machine learning model and data for configuring the machine learning model, according to one or more embodiments.

As an example, with respect to FIG. 2A, machine learning model 6 may take inputs 7 and provide outputs 8. In some embodiments, outputs 8 may be fed back to machine learning model 6 as input to train machine learning model 6 (e.g., alone or in conjunction with responses of the first user to messaging with one or more users of the first set of candidate users, labels associated with the inputs, or with other reference feedback information). In some embodiments, machine learning model 6 may update its configurations (e.g., weights, biases, or other parameters) based on its assessment of its prediction (e.g., outputs 8) and reference feedback information (e.g., responses of the first user to messaging with one or more users of the first set of candidate users, reference labels, or other information). In some embodiments, where machine learning model 6 is a neural network, connection weights may be adjusted to reconcile differences between the neural network's prediction and the reference feedback. Some embodiments include one or more neurons (or nodes) of the neural network requiring that their respective errors are sent backward through the neural network to them to facilitate the update process (e.g., backpropagation of error). Updates to the connection weights may, for example, be reflective of the magnitude of error propagated backward after a forward pass has been completed. In this way, for example, the machine learning model 6 may be trained to generate better predictions.

In some embodiments, one or more prediction models may initially be trained or configured to be targeted for one or more sets of candidate user classifications. For example, the candidate user classifications may include user attribute classifications, trigger classifications, occurrence classifications, and/or other classifications. For example, one or more sets of candidate user attribute classifications may include a set of candidate users that fall into one or more attributers groups such as personal relationship, location proximity, frequency of contact with the first user, health condition, symptoms, care plan, therapeutic activities, discussions with the first user, discussions of similar issues with other users, responsiveness, and/or other attribute classifications. In some embodiments, one or more sets of candidate user trigger classifications may include a set of candidate users that fall into one or more trigger type groups. In some embodiments, one or more sets of candidate user occurrence classifications may include a set of candidate users that fall into one or more occurrence type groups. In some embodiments, such prediction models may be stored in one or more database for later use. In some embodiments, based on a determination that a user falls under a particular set of user attribute classifications, a prediction model initially trained or configured to be targeted for that set of user attribute classifications may be selected, and an instance of the prediction model may be obtained and further trained or configured based on set of user attribute classifications. As an example, the prediction model may initially be trained or configured for users having a given medical condition and taking a given medication, and the prediction model may be selected for the first user based on the user being within the foregoing medical condition and medication group. To further personalize the system for the first user, an instance of the prediction model may be obtained and furthered trained or configured using data pertaining to the first user (e.g., trigger type and/or occurrence type). For example, the prediction model may predict that the first user will fail to perform a physical exercise because he often fails to perform that physical exercise, or will fail to take a medication on time because he often fails to take that medication on time. In some embodiments, the prediction model may be configured to predict factors that are predictive of a deviation from the regime. These predictive factors may be learned based on analyzing contextual parameters prior to the deviation of the therapeutic regime. For example, based on previous occurrences of deviation predictor triggers. In this way, for example, such prediction models may be specifically personalized for a given user, while reducing the amount of time and computational resources necessary to perform such personalization. As an example, because a prediction model is already pre-trained or configured for a larger set of users that already fall under one or more of the same classifications of the user, further personalization of the prediction model may be performed using a smaller training data set (e.g., smaller input training data, smaller reference feedback training data, etc.) than would otherwise have been required to achieve similar accuracy of predictions.

In some embodiments, one or more prediction models may initially be trained or configured to predict priority of the users in the set of candidate users for messaging with a user in connection with occurrence of a trigger associated with the user. For example, a prediction model may predict priority of each user of the first set of candidate users based on one or more attributes of the users, one or more trigger types, one or more occurrence types, and/or other priorities (e.g., predict ranking of the second users as described herein). In some embodiments, the prediction model may be updated based on training response data comprising data related to responses of the user to messaging with a user (e.g., the second user) having a higher priority than other users of the first set of candidate users. For example, training response data (e.g., including data related to responses of the user to messaging with the user having a higher priority) may be provided to the prediction model as reference feedback to train the prediction model in a second stage, and the prediction model may update one or more layers of the prediction model based on the training response data. Subsequent to the training of the prediction model, the first set of candidate users for messaging with a first user may be updated.

In some embodiments, system 10 is configured to access, based on the first occurrence of a first trigger, the first set of candidate users to initiate messaging between the first and one or more users of the first set of candidate users. For example, responsive to occurrence of the first trigger, system 10 is configured to prompt one or more users of the first set of candidate users to send a message to the first user. As another example, responsive to occurrence of the first trigger, system 10 is configured to generate a new thread associated with a user group comprising the first user and one or more users of the first set of candidate users (e.g., a conversation thread associated with the first user and the second user, a conversation threshold associated with the first user and the third user, etc.) or provide a prompt to one or more users of the first set of candidate users in one or more existing threads associated with the user group. In some embodiments, system 10 may be configured to send a prompt to the first available user from the candidate set (e.g., the system determines availability of the users before sending the prompt). In some embodiments, system 10 sends a prompt only to a threshold number of users (e.g., one user at a time) of the set of candidate users until a next prompting period (e.g., a 5-minute wait period, a 10-minute wait period, or other wait period before additional users may be prompted). In this way, for example, system 10 may reduce the number of prompts and messages from such users (e.g., by avoiding the transmission of additional prompts to other users to message the first user when it is determined that at least one user (or a threshold number of users) from the candidate set has messaged the first user in connection with the trigger occurrence), thereby saving network and other computational resources. In addition, as a result of the foregoing, system 10 may improve the user experience of the first user and the other users by mitigating the amount of messages received by the first user in connection with each trigger occurrence (e.g., so that the first user does not receive a large number of message every time the particular trigger occurs) and reducing the amount of prompts received by the other users in connection with each trigger occurrence (e.g., so that not all users of the first set of candidate users necessarily need to be prompted in connection with each trigger occurrence).

In one use case, for example, based on a priority (or ranking) of the second user (of the first set of candidate users), the second user may be selected for messaging with the first user prior to one or more other users of the first set of candidate users. For example, system 10 may initiate messaging between the first user and the second user based on the second user having a higher priority than the other users of the first set of candidate users. In some embodiments, system 10 may initiate messaging between the first user and the third user (of the first set of candidate users) based on the third user having a higher priority than one or more other users of the first set of candidate users and the second user being determined to be unavailable. For example, in case the second user fails to respond to the prompt to send a message (e.g., and is determined to be unavailable after a predetermined threshold amount of time has passed), system 10 may send a prompt to the third user having a higher priority than one or more other users of the first set of candidate users to send a message to the first user. In some embodiments, system 10 may be configured to send prompts including suggestions on messages to send the first user (e.g., based on type of messages that the positively responded to in the past).

In some embodiments, system 10 may be configured to determine a threshold amount of time that has passed since initiation of messaging between the first user and the second user (of the first set of candidate users) without obtaining a message from the second user in connection with the first occurrence of the first trigger (e.g., the threshold amount of time may include a specific time, a time interval of few minutes, hours, or days, or other time thresholds). In some embodiments, responsive to reaching the threshold amount of time, the system sends a prompt to the third user of the first set of candidate users (e.g., in case the same threshold of time or a different threshold of time related to the third user is reached, the system prompts a fourth user of the first set of candidate users, etc.). In some embodiments, system 10 may be configured to determine whether an initiation threshold for initiation of messaging between the first user and unavailable users has been reached without obtaining a message from one or more users of the first set of candidate users in connection with the first occurrence of the first trigger. For example, the initiation threshold may be initiation of messaging between the first user and a threshold number of unavailable users in connection with the first occurrence of the first trigger. For example, if a second user is unavailable, the system moves to the third user. If the third user is unavailable the system moves to the fourth user, etc.

In some embodiments, if system 10 determines that no one from the candidate set is available or another threshold number of such users is unavailable (e.g., without first sending a prompt to any of the candidate users), the system 10 may be configured to send a prior message to the first user. In some embodiments, responsive to the threshold amount of time, and/or the initiation threshold being reached, the system 10 may be configured to transmit a prior message of at least one user of the first set of candidate users to the first user in connection with the first occurrence of the first trigger. In some embodiments, system 10 may be configured to perform a query for one or more prior messages of one or more users of the first set of candidate users for transmission to the first user in connection with occurrence of the first trigger. For example, the prior messages may include messages that were sent to the first user in connection with a prior occurrence of the first trigger, messages that were sent in connection with occurrence of a different trigger but that the first user positively responded to, messages that were submitted by a user from the first set of candidate users but has not been received by the first user, messages that were sent to different users in response to occurrence of a similar trigger, messages that were sent to different users and the users were responsive to, and/or other prior messages. In this way, for example, even if one or more users of the candidate set is unavailable, the first user may nevertheless receive a relevant message in connection with the current trigger occurrence (e.g., a message that the first user will positively respond to).

In some embodiments, based on a determination that the first user has already received a threshold amount of messages (e.g., one message, a user-defined amount, or other threshold amount of messages) in connection with a given trigger occurrence, system 10 may determine to not deliver a message submitted by another user (e.g., a prompted user). In some embodiments, the message may instead be stored for future use. In response to a determination that no one from the first user's set of candidate users is available or another threshold number of users is unavailable, system 10 may deliver the stored message to the user. In one use case, for example, if messaging is initiated between the first user and five users (e.g., C1, C2, C3, C4, and C5) in response to occurrence of a given trigger, and a requested message is received from C1 and delivered to the first user prior to C3 submitting a message to be delivered to the first user, the transmission of C3's message to the first user may not be completed (e.g., after receiving C3's message, system 10 may not transmit the message to the first user) based on a determination that the first user has already received a sufficient number of messages. However, system 10 may transmit C3's message to the first user when the same or similar trigger occurs in the future (e.g., based on a determination that a threshold number of users are unavailable).

In some embodiments, system 10 comprises a therapeutic regime datastore 11, a user datastore 12, a monitor mechanism 13, an output mechanism 14, a receiver mechanism 15, and a ranking processor 16.

In some embodiments, the therapeutic regime datastore 11 is arranged to store therapeutic activity information including information on therapeutic activities forming part of the therapeutic regime of the first user. The user datastore 12 is arranged to store information on a plurality of second users. The second users in some embodiments are other users who may wish to send messages (e.g. messages of support or encouragement) to the first user regarding the first user's therapeutic regime. In some embodiments, the user datastore 12 is associated with a web portal 12*a* that can display information to second users.

The monitor mechanism 13 is arranged to monitor the first user to determine if the first user performs a therapeutic activity for which therapeutic activity information is stored in the therapeutic regime datastore. The monitor mechanism 13 is also arranged to produce an adherence result for that therapeutic activity based on the determination. Hence, the monitor mechanism 13 can determine if the first user adheres or does not adhere to the therapeutic regime by determining if the therapeutic activities in the therapeutic regime are performed.

The output mechanism 14 is arranged to output information to the second users regarding the adherence result. As will be discussed in more detail below, the output mechanism 14 can output information to the second users indicating whether the first user did or did not perform the therapeutic activity. In some embodiments, the output mechanism 14 is arranged to output the information to the second users regarding the adherence result using the web portal 12*a* via a suitable network (not shown), so that the second users can view the information regarding the adherence result via the web portal 12a. Other embodiments can use other ways of outputting the information regarding the adherence result to the second users (e.g. email or other suitable messaging means).

The output mechanism 14 is also arranged to output messages received from the second user to the first user. In some embodiments, the output mechanism 14 is arranged to output the messages to the first user using a display. Hence, in some embodiments, the output mechanism 14 comprises a display. Other embodiments can use other ways of providing a message to the user.

The receiver mechanism 15 is arranged to receive messages from the second users to the first user relating to the adherence result. For example, as discussed in more detail below, the received messages could be messages of support or encouragement from the second users to the first user.

In some embodiments, the ranking score relates to the likely influence of the said second user on the adherence of the first user to the therapeutic regime. In some embodiments, the likely influence between the second users and the first user may be measured quantitatively, based on at least one of a number of different factors relating to the interaction and interrelationship of the first user and a second user. The likely influence is representative of how influential a second user is on the first user, for example in terms of encouraging the first user to perform a certain task. The likely influence may be determined by considering an influence score for each of the number of different factors relating to the interaction and interrelationship of the first user and a second user. The ranking score may then in turn determined by taking all these different influence scores into account.

Hence, in such embodiments, the first user receives messages from the second users relating to the adherence result. As discussed in more detail below, in some embodiments, the messages are output to the first user in consideration of the ranking scores, so that messages from the most influential second users are ranked higher than messages from less influential second users. By doing this the first user is provided with messages (e.g., messages of support or encouragement) ranked according to how likely the messages are to be effective.

This helps ensure that the first user can be provided with messages (e.g., messages of support) from second users. The ranking of the messages from the second users and the output of the messages in consideration of this ranking ensures that the most important or most relevant messages are given the appropriate attention by the first user. This avoids the technical issue of the user having a great many messages to sift through to get to the important messages. It also helps ensure that important messages are not missed by the user.

In some embodiments, the therapeutic regime datastore 11, user datastore 12, monitor mechanism 13, output mechanism 14, receiver mechanism 15, and the ranking processor 16 are provided on the same apparatus. For example, such an apparatus could be a smart phone, tablet, general purpose computer or other suitable apparatus. In other embodiments, the apparatus may communicate with external additional monitoring mechanisms. Also, in other embodiments, the elements of the system could be provided on different devices.

In some embodiments, the monitor mechanism 13 can have local components distributed across several devices. Those could either communicate with a local control unit (represented by one of the monitoring devices or by a separate device) or with a remote system or both of these approaches can be combined in one system. In some embodiments, the monitor mechanism 13 can have a form of a remote system (e.g. web server) accessed by the user using a local terminal (e.g. computer, smartphone, tablet etc.), for instance for questionnaire based user monitoring.

In some embodiments, the monitor mechanism 13 can be in the same device as the output mechanism 14 or in separate devices (i.e. one device monitors the first user and another device displays messages to the first user).

In some embodiments, the monitor mechanism 13 and/or the output mechanism 14 can be in the same device as the user datastore 12 or in separate devices (e.g. one device monitors the first user and another device stores information on the second users).

Furthermore, in some embodiments, the output mechanism 14 can have local components distributed across several devices. For example, one component could display a visual message, while another component could play an audible component. In some embodiments, the output mechanism 14 can display the messages from the second user via a number of different mechanisms, e.g. via a number of different local components.

In some embodiments the monitor mechanism 13 can actively monitor the user. In other embodiments the monitoring of the can be based on self-report in which the monitor mechanism 13 could rely on the user's input to determine if the therapeutic activity is performed. In other embodiments, the monitor mechanism 13 can rely on a combination of both.

Figure 3:
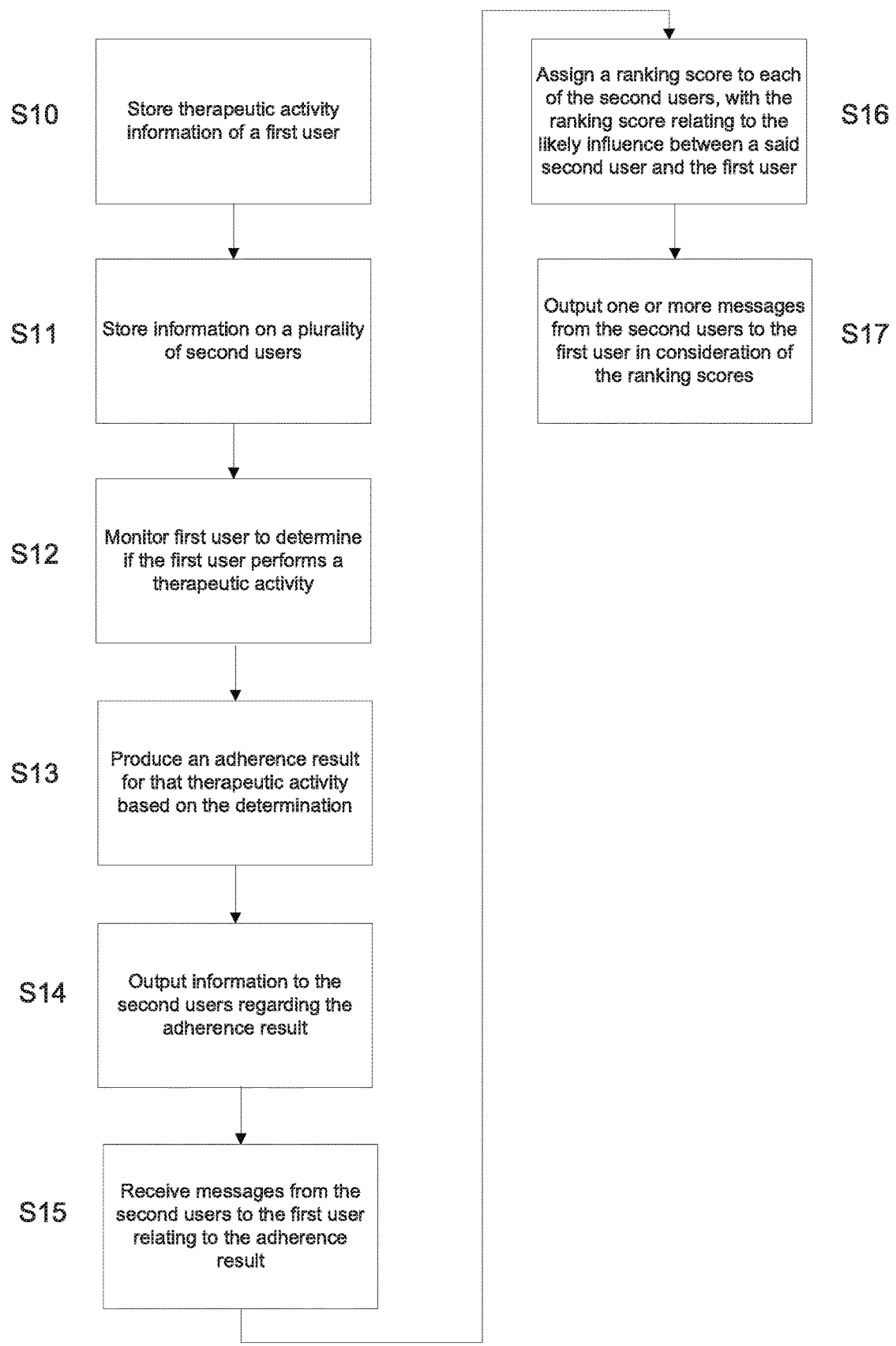
FIG. 3 shows a flow diagram explaining the operation of the system according to one or more embodiments.

FIG. 3 shows a flow diagram explaining the operation of the system 10. In this explanation, as an example, a first user with Crohn's disease will be considered.

Crohn's disease is an autoimmune disease, and patients typically take oral medication. A contemporary and very powerful treatment involves biologics, which have to be self-injected typically every two to three weeks. Failure to do so, i.e. longer gaps between injections or stopping the injection in symptom-free periods leads to reactivation of the disease as a result of excessive TNF-alpha particles in blood causing inflammatory reactions of sensitive body tissues. This causes the affected body parts (for Crohn's disease these are intestines) to be gradually damaged by the inflammation and lose their function, requiring surgical intervention.

In step S10 of FIG. 3, the system 10 stores therapeutic activity information of the first user in the therapeutic regime datastore 11. In this example, the first user with Crohn's disease has a therapeutic regime that comprises the therapeutic activity of self-injecting biologics every two weeks. Hence, the therapeutic regime datastore 11 stores that the first user must self-inject biologics every two weeks.

In this example, the therapeutic regime datastore 11 stores that biologics must be self-injected at intervals of 13-15 days (i.e. two weeks plus or minus a day). Hence, once the user has self-injected one set of biologics, the therapeutic regime datastore 11 will indicate that the biologics should be self-injected in a time window of 13 to 15 days. If the therapeutic activity of self-injecting the biologics is carried out before 13 days, then the therapeutic regime is inefficient. If the therapeutic activity of self-injecting the biologics is carried out after 15 days, then the therapeutic regime is ineffective. In this example, adherence to the therapeutic regime means self-injecting the biologics at intervals of 13-15 days.

In some embodiments, the system 10 determines the therapeutic activity information using data from a healthcare professional. In some embodiments, the therapeutic activity information could be determined via a questionnaire or by other means.

At step S11, the system 10 stores user information on a plurality of second users. The second users in some embodiments are other individuals that may wish to send messages to the first user regarding the first user's therapeutic regime. For example, the second users could include friends and family of the first user. The second users could also include other users that share the same or similar health condition as the first user, or other users that have a different health condition to the first user, but that need to carry out the same or similar therapeutic activities as the first user.

In some embodiments, the system 10 obtains the information about the second users from the web portal 12a via a suitable network (not shown). The web portal 12a obtains information provided by the first user on their friends and family, and information on the relationship between the second users and the first user is stored in the user datastore 12.

In some embodiments the user datastore 12 also stores details of other users, who do not have a pre-existing relationship with the first user. Such details include, in some embodiments, details of relevant health conditions of the users. This information can be provided via the web portal 12a. Hence, the system 10 can, via the user datastore 12, determine which other users have the same or similar health conditions to the first user. The system 10 could also, via the user datastore 12, determine which other users need to carry out the same or similar therapeutic activities as the first user. The similarity of health conditions may be determined by establishing whether two health conditions belong in a same category, for example pulmonary, coronary, etc., and/or by comparing the number of shared symptoms between two health conditions. It would be appreciated that there many other ways in the relevant art for determining similarity of health conditions.

It will be appreciated that two users may have different health conditions, but need to carry out similar therapeutic activities. For example, there are a number of different conditions that require the therapeutic activity of self-injection. Hence, a first user who is struggling (e.g., for physiological reasons) with the therapeutic activity of self-injection for their Crohn's disease could find comfort from a message of support from a user who has overcome such difficulties in the therapeutic activity of self-injection—even if the other user needed to self-inject for a different reason.

In this example, the "second users" are selected by the system 10 to include those other users who are friends and family of the first user, those other users who have Crohn's disease, and those other users who need to self-inject as part of a therapeutic regime. It will be appreciated that for a large number of users stored in the user datastore 12, the numbers of such "second users" (i.e. friends and family, as well as those with similar health conditions/therapeutic activities) may be large.

Hence, it will be appreciated that in some embodiments, the number of second users (i.e. those other users who receive details of the therapeutic activities of the first user) may be limited. For example, in some embodiments, the number of other users with similar health conditions/therapeutic activities could be limited by imposing a geographical restriction (e.g. those who live within 10 miles) or using some other type of filter. Such filtering of the users with similar health conditions/therapeutic activities could be done in a number of ways.

In other embodiments, all potential users of the system could receive details of the therapeutic activities of the first user, and the ranking processor 16 (discussed in more detail below) could be used to rank the messages from the second users in a suitable way to ensure that the most relevant messages are displayed more prominently to the first user. As a result, even if a large number of messages are sent to the first user by a large number of second users, the ranking of the second users will ensure that messages from the most important or most influential second users (which may also take into account the context and/or content of the messages) will be displayed to the first user more prominently.

It will be appreciated that although step S11 is shown after S10, this is purely for convenience of illustration. The system 10 could store the therapeutic activity information before, after or simultaneously as it stores the user information on a plurality of second users.

In some embodiments, the output mechanism 14 outputs reminder information to the first user in the time window (i.e. 13-15 days since the last self-injection) to carry out the therapeutic activity.

At step S12, the monitor mechanism 13 monitors the first user to determine if the first user performs a therapeutic activity for which therapeutic activity information is stored in the therapeutic regime datastore. In this example, the monitor mechanism 13 receives a user indication from the first user when the user has self-injected the biologics.

At step S13, the monitor mechanism 13 produces an adherence result for that therapeutic activity based on the determination in step S12.

In this example, if the user has self-injected the biologics at the correct time (i.e. at intervals an interval of 13-15 days) since the previous self-injection, then the adherence result will indicate that the first user correctly performed the therapeutic activity, and that the first user is thus adhering to the therapeutic regime. In this example, if the user has self-injected the biologics too early (i.e. before 13 days) since the previous self-injection, then the adherence result will indicate that the first user incorrectly performed the therapeutic activity, and that the first user is thus not adhering to the therapeutic regime. Furthermore, if it is more than 15 days after the last self-injection and the monitor mechanism 13 has not received a user indication from the first user that the user has self-injected the biologics, then the monitor mechanism 13 can determine that the first user is late with the self-injection, and thus is not adhering to the therapeutic regime.

Hence, in this example, the adherence result can indicate: 1) that the first user correctly performed the therapeutic activity; 2) that the first user incorrectly performed the therapeutic activity by self-injecting too early; 3) that the first user incorrectly performed the therapeutic activity late by missing the optimum window for self-injecting.

At step S14, the output mechanism 14 outputs information to the second users regarding the adherence result. In some embodiments, the output mechanism 14 sends information to the web portal 12a via a network (not shown), where it can then be displayed to the second users.

In some embodiments, the second users view the information regarding the adherence result via the web portal 12a and can write messages to the first user to support adherence to the therapeutic regime. In some embodiments, the second users can use the web portal 12a to write the messages.

At step S15, the receiver mechanism 15 receives messages from the second users to the first user relating to the adherence result. For example, if the adherence result indicates that the first user correctly performed the therapeutic activity, then the messages from the second users could be congratulatory in nature, encouraging the first user to continue adhering to the therapeutic regime.

If the adherence result indicates that the first user incorrectly performed the therapeutic activity by self-injecting too early, then the messages from the second users could encourage the first user to self-inject within the therapeutic time window the next time (i.e. in another 13-15 days).

If the adherence result indicates that the first user incorrectly performed the therapeutic activity by missing the optimum window for self-injecting, then the messages from the second users could encourage the first user to self-inject as soon as possible—hence acting as a further reminder to the first user to carry out the therapeutic activity.

If the adherence result indicates that the first user incorrectly performed the therapeutic activity late by self-injecting after the optimum window for self-injecting, then the messages from the second users could encourage the first user to self-inject on time next time.

It will be appreciated that such messages, for example from a second user with the same health condition who suffered an onset event as a consequence of not adhering to the same therapeutic regime could be a very influential on the first user.

At step S16, the ranking processor 16 is arranged to assign a ranking score to each of the second users, with the ranking score relating to the likely influence between a said second user and the first user. In some embodiments, the ranking score relates to the likely influence of the said second user on the adherence of the first user to the therapeutic regime.

As discussed, the second users are selected by the system 10 to include those other users who are friends and family of the first user, those other users who have Crohn's disease, and those other users who need to self-inject as part of a therapeutic regime. It will be appreciated that for a large number of users stored in the user datastore 12, the number of second users sending messages to the first user may be large. This presents a problem that the user will be sent a large number messages, which in conventional messaging systems would be just displayed by such systems in a list (e.g. in date order).

In some embodiments, the ranking processor 16 uses both the relationship between the second users and the first user (inter-relational ranking) and the context of the message (contextual ranking) to rank the second users. Hence, the ranking by the ranking processor 16 is used to rank the messages received from the second users, which enables the most relevant messages to be displayed more prominently to the first user.

In this example, those second users who are friends and family of the first user will receive a high interrelational ranking, as they have a close relationship to the user. Those second users who the first user does not have a previous relationship with will have a low inter-relational ranking. In the absence of other factors, messages from friends and family of the first user can be assumed to have a higher impact on the behavior of the first user than messages from strangers.

In this example, the contextual ranking will depend on the adherence result. For example, if the adherence result indicates that the first user correctly performed the therapeutic activity by self-injecting in the time window, then the messages from the second users are likely to be congratulatory in nature, and in this context, messages from friends and family of the first user are likely to be most effective as messages of support—because the congratulations will be coming from a friend or family member.

However, if the adherence result indicates that the first user incorrectly performed the therapeutic activity by self-injecting either too early or by missing the time window, then a message from a second user with the same health condition who has firsthand experience of non-adherence may be very effective as a message of support and encouragement. This is because, in this context, the message from such a second user with knowledge of the health condition could have higher impact on the behavior of the first user than a messages from someone (even if a familiar member) with no knowledge of the health condition.

As a result, the ranking processor 16 can rank the second users according to how effective their messages are likely to be on promoting adherence to the therapeutic regime of the first user. The balance between interrelational ranking and contextual ranking (and other potential ranking factors discussed below) will depend on the embodiment and the specific health condition and therapeutic activity.

In some embodiments, the user datastore 12 is arranged to store information on the relationships between the plurality of second users and the first user, and the ranking processor 16 is arranged to assign higher ranking scores to those second users with closer relationships to the first user. For example, the "closeness" of the relationship may be determined according to: similarities in health conditions, whether a second user is a family member, friend, or acquaintance. This information may be obtained using a survey. In some embodiments, the user datastore 12 is arranged to store information on health conditions of the second users, and the ranking processor 16 is arranged to assign higher ranking scores to those second users with similar health conditions to the health condition of the first user.

Furthermore, the user datastore 12 is arranged to store information on therapeutic activities carried out by the second users, and the ranking processor 16 is arranged to assign higher ranking scores to those second users who carry out similar therapeutic activities to the therapeutic activity of the first user. In some embodiments, the ranking processor 16 is arranged to assign different ranking scores to the second users depending on the nature of the adherence result. The nature of the adherence result may be indicative of how well the first user performed the therapeutic activity. There may be many possibilities of how the nature of adherence result is influential on the assignment of ranking scores for the second users.

Hence, a message from a friend with the same health condition who needs to carry out the same therapeutic activity (and thus who would have interrelational ranking and high contextual ranking) would be ranked higher than a message from a second user unknown to the first user with an unrelated health condition.

At step S17, the output mechanism 14 outputs one or more messages from the second users to the first user in consideration of the ranking scores. In some embodiments, the output mechanism 14 outputs received messages from the second users to the first user, giving priority to messages from those second users who are ranked highly.

In some embodiments, the output mechanism 14 is arranged to display the messages to the first user on a display. Instead of displaying a list of messages in, for example, time/date order (as in conventional systems), in some embodiments the output mechanism 14 is arranged to display a list of received messages from second users, with the messages from the highest ranked second users displayed at the top of the list and in a larger font. As a result of this, the received messages from the highest ranked second users will be displayed the most prominently.

It will be appreciated that the receiver mechanism 15 could receive a large number of messages from second users. In a conventional system in which messages are displayed in time/date order, then the first user will be provided with a long list of messages, some of which will be more relevant than others. By ranking the second users in this way, the received messages from the most relevant second users (i.e. the highest ranked) will be displayed the most prominently. This maximizes the effect of the received messages and helps ensure that the first user reads the most important messages.

Hence, an important benefit of the system 10 as described above is that messages from the more relevant second users will be output in a more preferential way (e.g. at the top of the list and/or in a bigger font) than messages from less relevant second users.

In some embodiments, the output mechanism 14 outputs one or more messages from the second users to the first user in consideration of the ranking scores as the messages from the second users are received. However, as discussed in more detail later, the delivery of the messages can be scheduled to optimize the effectiveness of the message. For example, the time of delivery of message to the first user can be scheduled according to message contents and previous or historical sequence of adherence event(s).

In some embodiments, the output mechanism comprises a number of devices capable of outputting the messages to the first user. In such embodiments, the ranking processor can be arranged to determine which of these devices to use to output each message to the first user based on the therapeutic activity to which each message relates to. Hence, in such embodiments, the delivery mechanism for the messages can be determined based on the ranking of the second users to optimize the effectiveness of the messages. This provides another way in which received messages from the most relevant second users (i.e. the highest ranked) can be displayed the most prominently (e.g. on the most prominent/noticeable output device).

The ranking of the second users can be done in a number of ways, with the balance between different ranking factors discussed depending on the embodiment and the specific health condition and therapeutic activity.

In some embodiments, the user datastore 12 is arranged to store information on the proximity between the plurality of second users and the first user, and the ranking processor 16 is arranged to assign higher ranking scores to those second users who live closest to the first user. In some embodiments, the location proximity between the plurality of second users and the first user may be measured in terms of the distance between the first user and a second user.

In some embodiments, the user datastore 12 is arranged to store information on the frequency of contact between the each of the second users and the first user, and the ranking processor 16 is arranged to assign higher ranking scores to those second users with more frequent contact with the first user.

The frequency of contact between the each of the second users and the first user could be determined by interactions (e.g. messages sent/received) via the web portal 12a.

The frequency of contact between the each of the second users and the first user could be determined in other ways, such as whether the first user viewed a profile of the second user stored on the web portal 12a. In some examples, the web portal 12a could have a message board facility, and the frequency of contact between the each of the second users and the first user could be determined whether the first user liked (or otherwise up-rated) messages from the second user on the message board of the web portal 12a. The frequency of contact between the each of the second users and the first user could be determined by analyzing other communication (including liking or otherwise up-rating messages) on social networks.

In some embodiments, the user datastore 12 is arranged to store information on the frequency of physical contact between the each of the second users and the first user, and the ranking processor 16 is arranged to assign higher ranking scores to those second users with more frequent physical contact with the first user. The frequency of physical contact between the each of the second users and the first user could be determined in a number of ways, for example by analyzing message histories or social media interaction.

In some embodiments, the monitor mechanism 13 is arranged to determine how long the first user spends viewing messages from each of the second users, and this information is stored in the user datastore 12. In such embodiments, the ranking processor 16 can be arranged to assign higher ranking scores to those second users whose messages are viewed for longer by the first user. In some embodiments, the assignment of ranking scores is performed subsequent to the initial output of messages from second users. For example, as discussed, the web portal 12a could have a message board facility, and the monitor mechanism 13 is arranged to determine how long the first user spends viewing messages made by each of the second users on the message board facility.

In some embodiments, the system 10 can further comprise a user input arranged to receive an input from the user indicating how useful the first user found each message from the second users in aiding adherence to the therapeutic regime. In such embodiments, this input can be used in the determining of the ranking scores. Second users whose messages have been considered to be useful in the past could be ranked higher.

In some embodiments, the ranking processor 16 is arranged to assign different ranking scores to the second users depending on the content of the messages sent by the second users. In other words, the ranking processor 16 can analyze the content of the messages received from the second users (e.g. by determining if the messages contain certain keywords) and can assign higher rankings to messages that are considered to be more relevant. For example, a message from a family member including the term "injection" is likely to be very relevant to the first user who needs to perform self-injection in the above example.

In some embodiments, the second users can send messages directly to the device of the first user, for example, not via a web portal but via an alternative messaging system such as email, SMS or other such messaging system. In some embodiments, the ranking processor can use the communications method used by the second users to send messages to the first user in the ranking.

For example, consider a situation in which the first user has indicated a preference for using a video chat service, for example because the first user likes video chatting with other users about their health condition. In such a situation, if a second user sends a message to the first user via a messaging system associated with the video chat service preferred by the first user, then that second user could be ranked higher than they otherwise would be.

In this some embodiments, if no messages are received from any second users, the output mechanism 14 is arranged to output a message prompt to second users to send messages.

In some embodiments, the ranking processor 16 is arranged to compare the ranking scores of those second users for which messages are received with a stored threshold. If the ranking scores of those second users for which messages are received are below the stored threshold, the output mechanism 14 is arranged to output a message prompt to second users whose ranking scores are above the stored threshold. Hence, in such embodiments, the system can issue prompts to ensure that highly ranked second users send messages of support to the first user.

In some embodiments of the invention, a patient (i.e. the first user) consents to sharing aspects of a care plan (i.e. a therapeutic regime) with third parties (i.e. second users). The second users can be sign up through the web portal 12a to receive updates for first user. The second users then receive a copy of aspects of care plan. Medication adherence events (i.e. therapeutic activities) are identified and posted together on the web portal 12a with regular updates on medication adherence. Then the likely influence of second users to the first user is determined. The second users then contribute messages of support to the first user. If influential second users are initially unavailable, then they could be prompted to leave a message. Messages received from second users are then ranked according to (i) the overall influence of the second user and (ii) the contextual influence of the message. The delivery of the messages is then scheduled, and the time of delivery of message to the first user is scheduled according to message contents and previous or historical sequence of adherence event(s). Until the scheduled time of delivery, the system can collect more message during time window when messages can be delivered. The selected messages are communicated over time through the output means 14. In embodiment, in which the output means comprises a number of devices, then the communication device which—at the time the message is communicated—has most contextual influence with the patient is chosen for delivery of the message.

Figure 4:
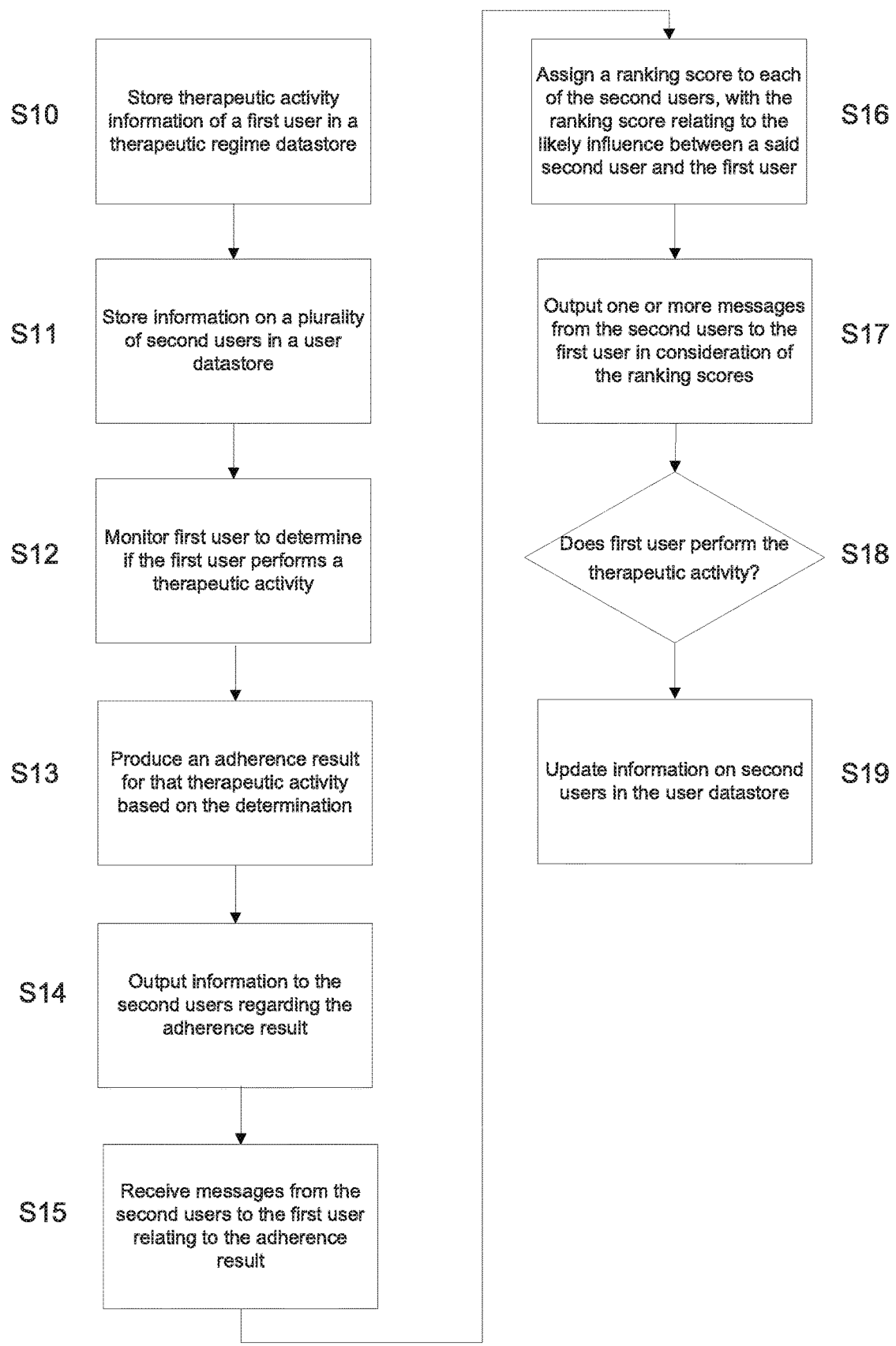
FIG. 4 shows a flow diagram explaining the operation of the system according to one or more embodiments.

FIG. 4 shows a flow diagram explaining the operation of the system 10 in another embodiment of the invention. As for FIG. 3, some embodiments will be explained by way of an example in which the first user Crohn's disease, and who must self-inject biologics at intervals of 13-15 days.

In some embodiments, the monitor mechanism 13 is arranged to determine if the therapeutic activity is subsequently performed by the first user following the output of a message from one of the second users to the first user. Following this, the user datastore 12 is arranged to store information on which second users' messages are effective in causing the therapeutic activity to be performed following the output of the messages. The ranking processor 16 can then use this information to assign higher ranking scores to those second users whose messages are effective in causing the therapeutic activity to be performed following the output of the messages. In some embodiments, the assignment of high ranking scores to those second users whose messages are effective is performed subsequent on the initial output of the messages.

Steps S10 to S17 of FIG. 4 are the same as for FIG. 3. As a result, in step S17, the output mechanism 14 outputs one or more messages from the second users to the first user in consideration of the ranking scores.

At step S18, the monitor mechanism 13 determines if the first user performed the therapeutic activity following the output of the messages from the second users. In this example, the monitor mechanism 13 receives a user indication from the first user when the user has self-injected the biologics, for example via a suitable user interface.

At step S19, the user datastore 12 is updated by the system to store information on which second users' messages are effective in causing the therapeutic activity to be performed following the output of the messages. A message from a second user whose previous message was effective in causing the first user to carry out the therapeutic activity is likely to be effective.

In some embodiments, the system can check to see if the user reads the second users' messages, and can update the rankings following the first user carrying out the therapeutic activity only for those second user's whose messages were read.

Figure 5:
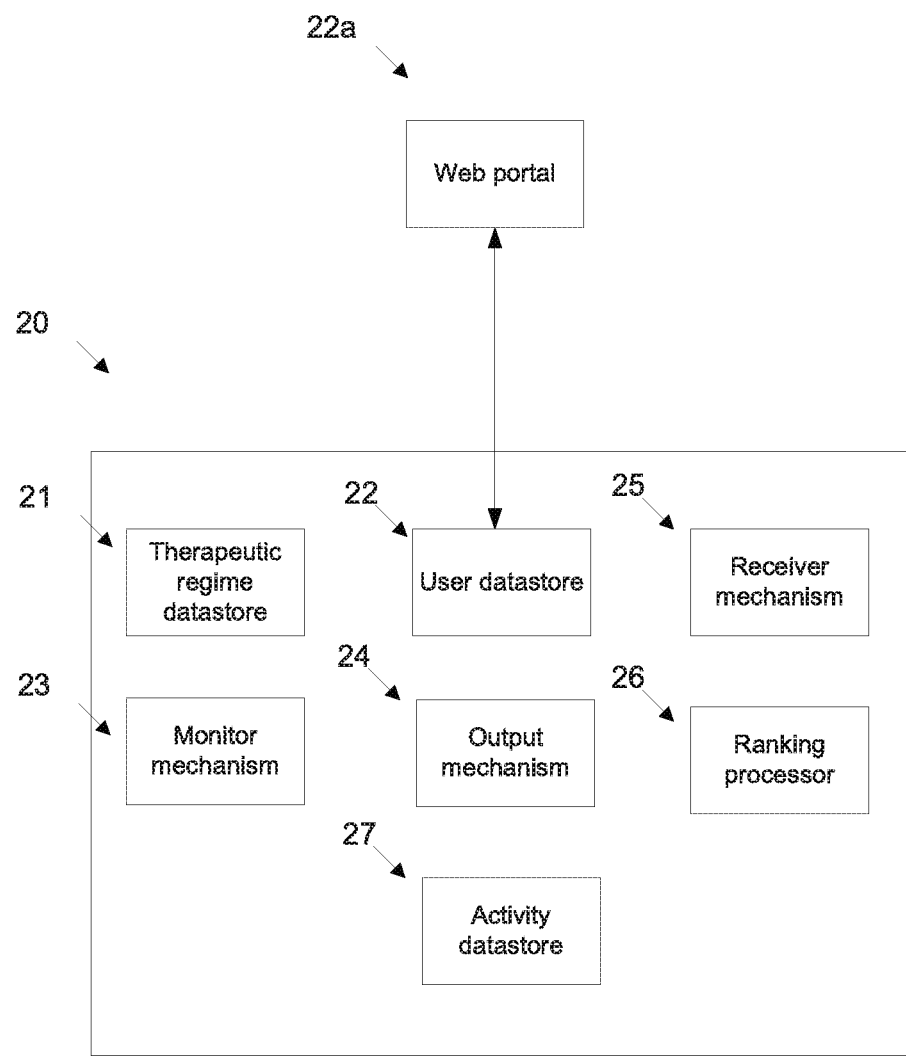
FIG. 5 schematically shows a system for messaging a user according to according to one or more embodiments.

FIG. 5 schematically shows a system 20 for messaging a user according to a third embodiment of the invention. In some embodiments, the system could be used by a first user with a long term health condition, with the first user having a therapeutic regime comprising a number of therapeutic activities that the user should perform to adhere to the therapeutic regime.

The system 20 comprises a therapeutic regime datastore 21, a user datastore 22, a monitor mechanism 23, an output mechanism 24, a receiver mechanism 25, a ranking processor 26, and a non-therapeutic activity datastore 27. In some embodiments, the user datastore 22 is associated with a web portal 22a that can display information to second users.

The therapeutic regime datastore 21 is arranged to store therapeutic activity information including information on therapeutic activities forming part of the therapeutic regime of the first user. In some embodiments, the therapeutic regime datastore 21 is part of the memory or other storage unit of the smart phone, and the therapeutic activity information including information on therapeutic activities forming part of the therapeutic regime of the first user could be received via the web portal 22a.

The user datastore 22 is arranged to store information on a plurality of second users. The second users in some embodiments include other users who may wish to send messages (e.g. messages of support or encouragement) to the first user regarding the first user's therapeutic regime. In some embodiments, the user datastore 22 is associated with a web portal 22a that can display information to second users.

The monitor mechanism 23 is arranged to monitor the first user to determine if the first user performs a therapeutic activity for which therapeutic activity information is stored in the therapeutic regime datastore 21. The monitor mechanism 23 is also arranged to produce an adherence result for that therapeutic activity based on the determination.

The output mechanism 24 is arranged to output information to the second users regarding the adherence result. In some embodiments, the output mechanism 24 is arranged to output the information to the second users regarding the adherence result using the web portal 22a via a suitable network (not shown), so that the second users can view the information regarding the adherence result via the web portal 22a. The output mechanism 24 is also arranged to output messages received from the second user to the first user. In some embodiments, the output mechanism 24 is arranged to output the messages to the first user using a display.

The receiver mechanism 25 is arranged to receive messages from the second users to the first user relating to the adherence result.

The ranking processor 26 is arranged to assign a ranking score to each of the second users, with the ranking score relating to the likely influence between the second users and the first user. In some embodiments, the ranking score relates to the likely influence of the said second user on the adherence of the first user to the therapeutic regime.

The non-therapeutic activity datastore 27 is arranged to store information regarding non-therapeutic activities that could be carried out by the first user. As described in more detail below, the non-therapeutic activity information is used by the monitor mechanism 23 to monitor the user, so as to enable messages from the second users to be delivered at an optimum time, e.g. by delivering a message when the user is carryout out (or not carrying out) certain non-therapeutic activities. The non-therapeutic activity information can be set by the user or by a third party.

The term "non-therapeutic activity" is used herein in the broad sense, to encompass any activity that the user may be engaged in or any state of the user. The non-therapeutic activity could relate to an action of the user (e.g. watching television) or a passive activity (e.g. being at a certain location).

Figure 6:
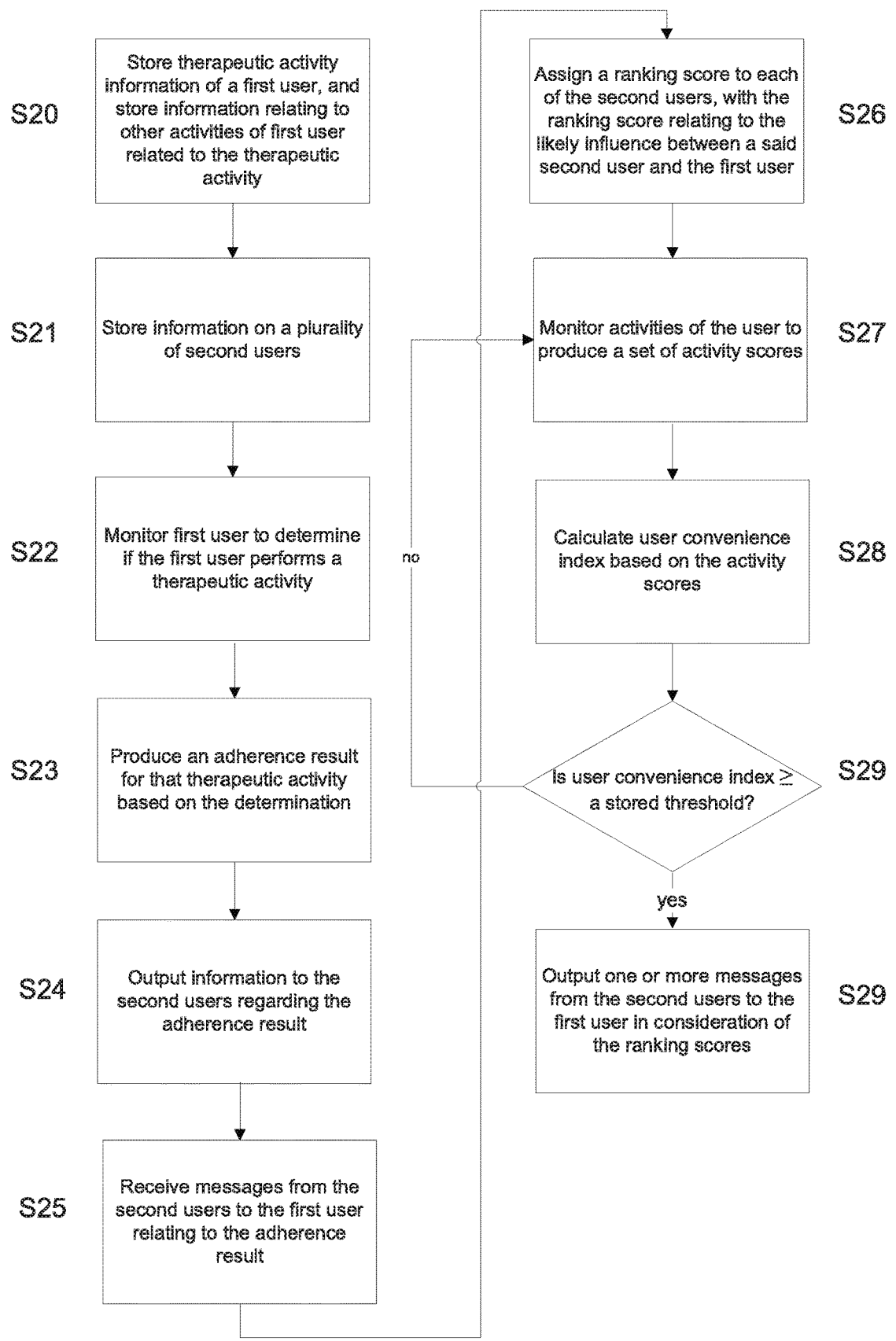
FIG. 6 shows a flow diagram explaining the operation of the system according to one or more embodiments.

FIG. 6 shows a flow diagram explaining the operation of the system 20. In this explanation, as an example, a first user with Chronic obstructive pulmonary disease (COPD) disease will be considered.

Chronic obstructive pulmonary disease (COPD) is the occurrence of chronic bronchitis or emphysema, a pair of commonly co-existing diseases of the lungs in which the airways become narrowed. This leads to a limitation of the flow of air to and from the lungs, negatively impacting gas exchange and causing shortness of breath (dyspnoea).

For COPD the daily oral medication is complemented by daily inhalation medication (long-acting bronchodilators with steroids), symptom based inhalation medication (short acting bronchodilators) used in case of shortness of breath and for severe cases with oxygen therapy and non-invasive ventilation.

Not taking bronchodilators leads to shortness of breath and higher sensitivity of the lung tissues to infections and external stimuli, leading further to COPD acute exacerbation, requiring an emergency room visit. Roughly 30% of those emergency room visit result in the hospitalization of the patient, with roughly 10% of those hospitalizations being mortal.

Not using oxygen therapy leads to hypoxemia or hypercapnia, which could cause loss of consciousness, irreversible damage of brain cells or respiratory failure. The latter always requiring hospitalization and highly mortal, the former two very dangerous and having long term irreversible effect on quality of life.

In step S20 of FIG. 6, the system 20 stores therapeutic activity information of the first user. In some embodiments, the system 20 determines the therapeutic activity information using data from a healthcare professional, for example via a suitable network.

In step S20 of FIG. 6, the system 20 also stores a selection of user activities to monitor the user as non-therapeutic activity information in the non-therapeutic activity datastore 27. The non-therapeutic activity information comprises a selection of activities that could be carried out by the user that are considered likely to have an effect on the efficacy of a message sent by a second user. As discussed below, monitoring the non-therapeutic activities of the user is very useful when considering when to output messages to the first user. For example, a message from the second user is intended to be a prompt to carry out a therapeutic activity (i.e. act as a reminder), then delivering the message at an optimum time will maximize the effectiveness of the message.

For example, if the therapeutic activity associated with the message from a second user is a message aimed to encourage the first user to perform their oxygen therapy (e.g. after a missed therapeutic activity), then the efficacy of the message from the second user associated with that therapeutic activity may be increased if the message is delivered when the user is relaxed and at home. In contrast, the efficacy of the message associated with that therapeutic activity may be decreased if the message is delivered when the user is doing a non-interruptible task such as making a telephone call.

In some embodiments, the system 30 determines the non-therapeutic activity information using a user input. In other words, the user enters a set of non-therapeutic activities that are relevant to how likely they are to perform the therapeutic activity, along with an indication whether the non-therapeutic activity is considered to be likely to have a positive or negative effect on how likely there are to perform the therapeutic activity.

Steps S21 to S26 are equivalent to steps S11 to S16 of FIG. 3, and will not be described in detail.

At step S27, the monitor mechanism 23 of system 20 monitors the user using the non-therapeutic activity information. In other words, the monitor mechanism 23 monitors whether the user is carrying out the non-therapeutic activities included in the non-therapeutic activity information. In some embodiments, the monitor mechanism 23 determines if each activity in the non-therapeutic activity information is being carried out, and then assigns a set of activity scores.

A step S28, the monitor mechanism 23 calculates a user convenience index using the activity scores. In some embodiments, the user convenience index is a monitoring result that is a sum of the activity scores. In other embodiments, the monitor mechanism 23 can determine the monitoring result in other ways.

Then, at step S29, the ranking processor 26 calculates whether the user convenience index is greater than or equal to a threshold. If the user convenience index is greater than or equal to the threshold, then, at step S29, the output mechanism 24 outputs one or more messages from the second users to the first user in consideration of the ranking scores. If the user convenience index is not above the threshold, then the monitoring of the activities the user using the activity information continues (step S27).

In some embodiments, the messages from the second users are displayed on the system 20 via the output mechanism 24 comprising a display. In other embodiments, the messages may be communicated in any of a variety of ways including audible, visual or tactile signals to a smart phone, nearby display, and the user of a wearable device.

To help explain steps S27, S28 and S29, an example scenario will be discussed in relation to the first user with Chronic obstructive pulmonary disease (COPD) disease. In this example, the first user has a smart phone acting as the device of the system 20. As discussed, COPD is associated with a number of therapeutic activities, and in this example oxygen therapy will be considered.

In this example, in step S20, the user is then presented with a list of non-therapeutic activities by the smart phone that can be monitored and that are relevant to the likelihood of the user performing the therapeutic activity. The user can then select those non-therapeutic activities from the list, and indicate whether those activities are likely to have a positive or negative impact on the likelihood of the user performing the therapeutic activity. In other embodiments, the system can determine which non-therapeutic activities are likely to have a positive or negative impact on the efficacy of the likelihood of the user performing the therapeutic activity automatically, for example by consulting a look-up table. Furthermore, such a look-up table could be dynamically updated taking into account how effective messages of support are at causing the therapeutic activity to be performed while the user is carrying out certain non-therapeutic activities.

In other embodiments, the relevance of the non-therapeutic activities can be determined based on whether those activities are likely to have a positive or negative impact on the efficacy of the message of support. For example, regardless of whether the message is a prompt to perform a therapeutic activity or not, there will still be relatively good and relatively bad times to deliver messages to the user based on what non-therapeutic activities the user is doing.

In some embodiments, the user may pick from a large selection of possible non-therapeutic activities. In other embodiments, the system may select appropriate non-therapeutic activities without a user input, for example based on a pre-stored set of criteria.

Figure 7:
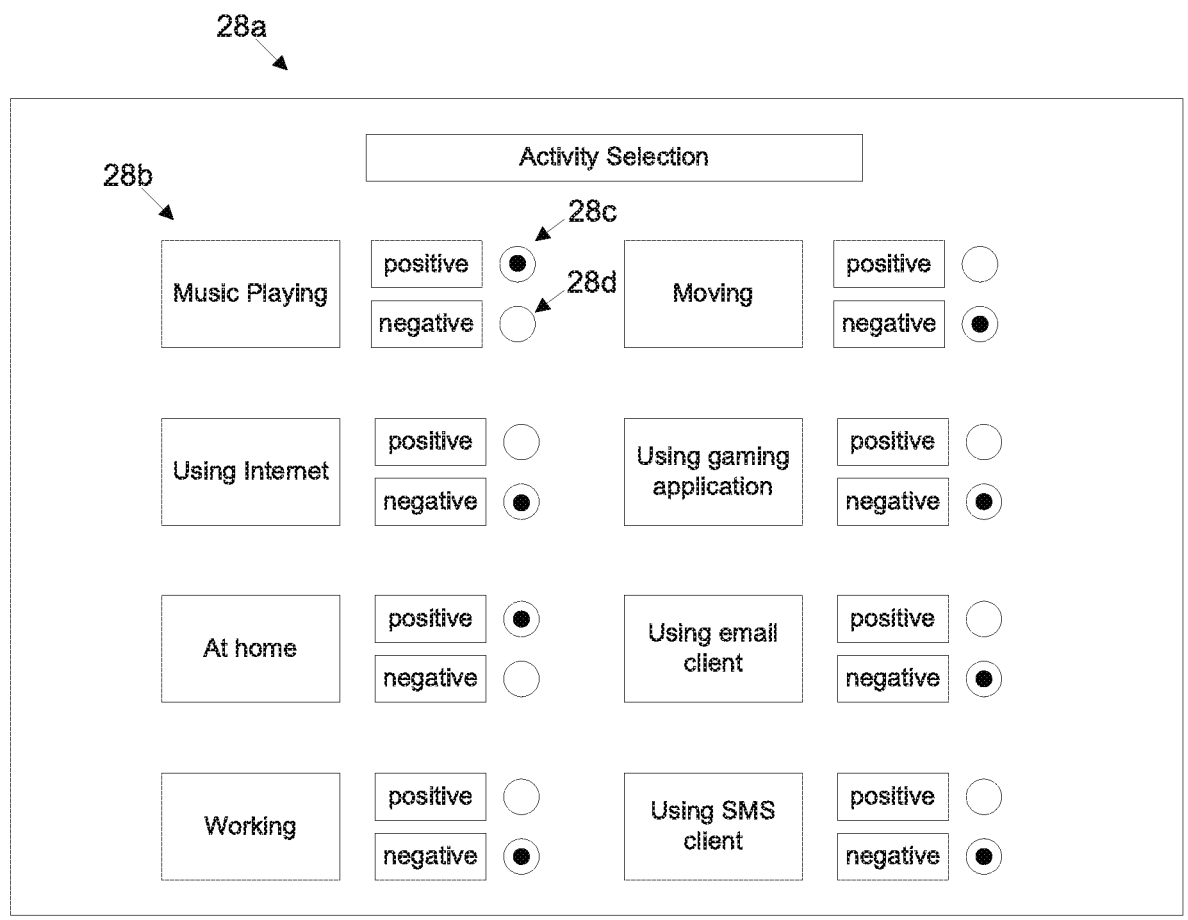
FIG. 7 shows a user interface for use according to one or more embodiments.

For example, the user could be presented with the non-therapeutic activities shown in FIG. 7. FIG. 7 shows an example user interface 28a for enabling the user to indicate which of a set of activities are considered likely to have a positive or negative impact on the likelihood of the user performing the therapeutic activity. In some embodiments, the user interface 28a would be displayed on the display of the system 20.

As shown in FIG. 7, the interface 28a shows a number of activities 28b, along with check boxes 28c and 28d that the user can user to indicate if they consider that these activities have a positive or negative effect on the likelihood of the user performing the therapeutic activity following a message from a second user. In some embodiments, not ticking a check box for an activity indicates that the user considers that activity has a neutral effect on the likelihood of the user performing the therapeutic activity.

If a non-therapeutic activity is considered to have a positive effect on the likelihood of the user performing the therapeutic activity, then the message from the second user (e.g. encouraging the first user to carry out the therapeutic activity) is likely to be more efficacious if that activity is being carried out when a message from the second user is output. If the non-therapeutic activity is considered to have a negative effect on likelihood of the user performing the therapeutic activity, then the message is likely to be less efficacious if that activity is being carried out when the message is output.

Each of these non-therapeutic activities would be monitored by the monitor mechanism 23 in an appropriate way for each activity. The activities in FIG. 3 are:

Music Playing: This indicates whether the system 20 is playing music. In this example, the user has indicated that this has a positive impact on the likelihood of the user performing the therapeutic activity (i.e. oxygen therapy in this example). This may be because, for example, the first user in general prefers to listen to music while performing the oxygen therapy. This activity could be monitored by the monitor mechanism 23 by determining if a music function of the system 20 is activated.

Using Internet: This indicates whether the system 20 is accessing the Internet. In this example, the user has indicated that this has a negative impact on the likelihood of the user performing the therapeutic activity. This may be because, for example, the first user prefers not to be distracted when using the Internet. This activity could be monitored by the monitor mechanism 23 by determining if a web browser function of the system 20 is activated.

At home: This indicates whether the system 20 is at the designated home location of the user. In this example, the first user has indicated that this has a positive impact on the likelihood of the user performing the therapeutic activity. This may be because, for example, the user prefers to carry out oxygen therapy while at home or because this is where the appropriate equipment is located. This activity could be monitored by the monitor mechanism 23 by using a GPS function of the system 20, or another suitable location function.

Working: This indicates whether the first user is working, for example using a work related application on the system 20. In this example, the first user has indicated that this has a negative impact on the likelihood of the user performing the therapeutic activity. This may be because, for example, the user prefers to carry out oxygen therapy while not working. This activity could be monitored by the monitor mechanism 23 by determining if the work related application on the system 20 is activated.

Moving: This indicates whether the system 20 is moving. In this example, the first user has indicated that this has a negative impact on the likelihood of the user performing the therapeutic activity. This may be because, for example, the user prefers to carry out oxygen therapy while seated. This activity could be monitored by the monitor mechanism 23 by using an accelerometer function of the system 20.

Using gaming application: This indicates whether the first user is using a gaming application. In this example, the first user has indicated that this has a negative impact on the likelihood of the user performing the therapeutic activity. This may be because, for example, the user prefers not to be interrupted with playing games. This activity could be monitored by the monitor mechanism 23 by determining if a gaming application on the system 20 is activated.

Using email client: This indicates whether the user of system 20 is using an email client on the system 20. In this example, the user has indicated that this has a negative impact on the likelihood of the user performing the therapeutic activity. This may be because, for example, the user prefers not to be interrupted with sending or reading emails. This activity could be monitored by the monitor mechanism 23 by determining if the email client on the system 20 is activated.

Using SMS client: This indicates whether the user of system 20 is using an SMS client on the system 20. In this example, the user has indicated that this has a negative impact on the likelihood of the user performing the therapeutic activity. This may be because, for example, the user prefers not to be interrupted with sending or reading SMS messages. This activity could be monitored by the monitor mechanism 23 by determining if the email client on the system 20 is activated.

Furthermore, in some embodiments, there are other non-therapeutic activities that have pre-stored influences on likelihood of the user performing the therapeutic activity, without requiring a user input. For example, the system 20 is arranged to store that making a telephone call using the system 20 has a negative impact on the likelihood of the user performing all therapeutic activities. Hence, for the non-therapeutic activity of "making a call" it is not necessary to present the user with an option for choosing whether the activity has a positive or negative impact, as it is always considered to have a negative impact. Such non-therapeutic activities could always be present in the non-therapeutic activity information, regardless of whether the user is given a choice of which other activities comprise the activity information.

Hence, at step S20, the user's preferences for each selected activity, along with any non-therapeutic activities whose influences on efficacy is predefined, are stored as non-therapeutic activity information in the non-therapeutic activity datastore 27.

At step 27, the monitor mechanism 23 monitors each of the selected activities, and at step S28 a user convenience index is calculated based on the monitoring. The user convenience index is calculated by considering the sum of the positive and negative influences on the likelihood of the user performing the therapeutic activity.

In some embodiments, an activity score is determined for each non-therapeutic activity, with the user convenience index being a sum of the activity scores. In some embodiments, if an activity whose influence is positive is being performed, then an activity score of 1 is given. If a non-therapeutic activity whose influence is negative is being performed, then an activity score of −1 is given. If the activity is not being performed (regardless of whether positive or negative), or if the user indicated that the activity had a neutral influence (e.g. by not ticking either the positive or negative check box in FIG. 7), then an activity score of 0 is given.

To help illustrate this example, three example states of the user will now be discussed with references to Table 1.

In state 1, the user is listening to music, using the internet, while walking in the park. The user is therefore not at home, and is moving. The user is not working, and not using a gaming application, email client or SMS client.

In state 2, the user is at home sitting down (and thus not moving), while making a call; while not using the internet, not listening to music, and not using a gaming application, email client or SMS client.

In state 3, the user is at home sitting down (and thus not moving), using the internet; while not listening to music, not working, and not using a gaming application, email client or SMS client.

The activity scores and user convenience index associated with states 1, 2 and 3 are shown in Table 1.

TABLE 1

| Activity | Score in State 1 | Score in State 2 | Score in State 3 |
|---|---|---|---|
| Music Playing | 1 | 0 | 0 |
| Using Internet | −1 | 0 | −1 |
| At home | 0 | 1 | 1 |
| Working | 0 | 0 | 0 |
| Moving | −1 | 0 | 0 |
| Using gaming application | 0 | 0 | 0 |
| Using email client | 0 | 0 | 0 |
| Using SMS client | 0 | 0 | 0 |
| Making a call | 0 | −1 | 0 |
| User convenience index | −2 | 1 | 0 |

At step S29, the system determines whether the user convenience index is greater than or equal to the stored threshold. In this example, the stored threshold is 1. Hence, for states 1 and 3, the user convenience index is determined to be less than the stored threshold. Therefore, for states 1 and 3, the system continues to monitor the user (step S27).

For state 2, the user convenience index is determined to be equal to the stored threshold. Hence, the system progresses to step S29, and the reminder is output to the user to pay the utility bill.

Hence, in some embodiments, the user is presented with a message about a therapeutic activity at a time that is considered to be appropriate for that therapeutic activity. This is done by delivering the message when the first user is carryout out (or not carrying out) certain non-therapeutic activities that are considered to have a positive or negative effect on the likelihood of the first user carrying out the therapeutic activity.

This enables such embodiments of the invention to provide much more effective messages when compared to conventional systems that simply provide messages or reminders at an absolute time.

The messaging system according to some embodiments can be used to ensure that the message (e.g. acting as a reminder for a missed therapeutic activity) is delivered when the first user is likely to be receptive to the message. Moreover, the first user may establish a more positive association with the therapeutic activity of which he/she is reminded/messaged because the message does not come at an inconvenient moment which may be perceived as annoying, but rather at a moment that he/she can act upon it.

In the above example, the therapeutic activity (i.e. oxygen therapy) is not associated with a time period for carrying out the therapeutic activity. However, it will be appreciated that other therapeutic activities can be associated with a predetermined time window.

In the above example, in step S20, the user is presented with a list of non-therapeutic activities by the smart phone that can be monitored and that are relevant to the likelihood of the user performing the therapeutic activity. In other embodiments, the relevance of the non-therapeutic activities can be determined based on whether those activities are likely to have a positive or negative impact on the efficacy of the message of support. For example, regardless of whether the message is a prompt to perform a therapeutic activity or not, there will still be relatively good and relatively bad times to deliver messages to the user based on what non-therapeutic activities the user is doing.

As discussed above, in some embodiments, the system can comprise an activity datastore arranged to store non-therapeutic activity information comprising information on non-therapeutic activities that are considered to have an effect on the impact of the message. In some embodiments, the impact of the message relates to the likelihood of the first user performing the therapeutic activity.

In such embodiments, the monitor mechanism is arranged to monitor the user to determine if the user is performing one or more non-therapeutic activities for which non-therapeutic activity information is stored in the activity datastore and to produce a monitoring result based on the determination. The ranking processor is arranged to determine when to send the first user the one or more messages from the second users based on the monitoring result, and the ranking processor is arranged to compare the monitoring result to a stored parameter. The output mechanism is arranged to time the output the one or more messages from the second users to the first user on the basis of the comparison of the monitoring result and the stored parameter.

In some embodiments, the stored parameter is a threshold, and the output mechanism is arranged to output the one or more messages from the second users to the first user when the monitoring result meets or exceeds the threshold.

In some embodiments, the monitor mechanism is arranged to monitor each non-therapeutic activity in the non-therapeutic activity information, and to assign an activity score based on whether that activity is being performed.

In some embodiments the threshold for the monitoring result (e.g. user convenience index) is fixed. However, in other embodiments, the threshold may vary, either with time or as a result of another adjustment by the system 20. For example, in embodiments in which the therapeutic activity is associated with a predetermined time window, the threshold may be lowered towards the end of the predetermined time window, thus helping to ensure that the message is provided within the predetermined time window.

In other embodiments, the threshold may be varied by the system for other reasons. For example, the system 20 may monitor compliance with a message acting as a reminder (i.e. whether the message as a reminder was acted upon or ignored) and use this to vary the threshold.

In the above mentioned example, the possible activity scores for each activity are −1, 0 and 1, representing a simple positive, neutral (or activity not being performed) or negative effect on the efficacy of the reminder, with the monitoring result being the sum of the activity scores. However, in other embodiments, different activities can be associated with different weights, with the weights either being predetermined or set by the user. Hence, in such embodiments, when the user convenience index is calculated, it will take into account the differently weighted activity scores. Hence, in some embodiments, the monitor mechanism 23 is arranged to assign different weight values to different activities scores.

In some embodiments, the system 20 is arranged to determine if the therapeutic activity is performed following the output of the messages. For example, the system 20 may be able to monitor (e.g. using the monitor mechanism 23 or other monitoring equipment) that the therapeutic activity has been performed. The system 20 could also rely on a user input to determine if the therapeutic activity has been performed following the message.

In some embodiments, the system 20 may determine that the therapeutic activity for which the message relates has actually been performed before the reminder has been issued. In such scenarios, the system 20 may opt to not present the message to the user.

In embodiments in which the system 20 obtains information (either via a user input or by monitoring) that the therapeutic activity has been completed, the system 20 can store adherence information relating to the non-therapeutic activity activities being performed by the user at the time of the therapeutic activity being completed. For example, the system 20 could analyze what activities (whether they are the ones stored in S20 or other activities monitored by the system 20) the user was carrying out while the therapeutic activity was performed, and use this information to improve the outputs of the messages in an iterative way. For example, the system 20 could use the adherence information to adjust the weights of the activity scores, to add activities into the set of activities used to calculate the monitoring result (e.g. user convenience index), and/or to vary the threshold.

This is useful in many circumstances. For example, even though such embodiments of the invention provide messages that are more likely to be acted upon than conventional systems, it is still possible that the message will be ignored. By using the adherence information in this way, the system of such embodiments can adapt to the precise demands of the user in order to improve the efficiency of the messaging system.

Figure 8:
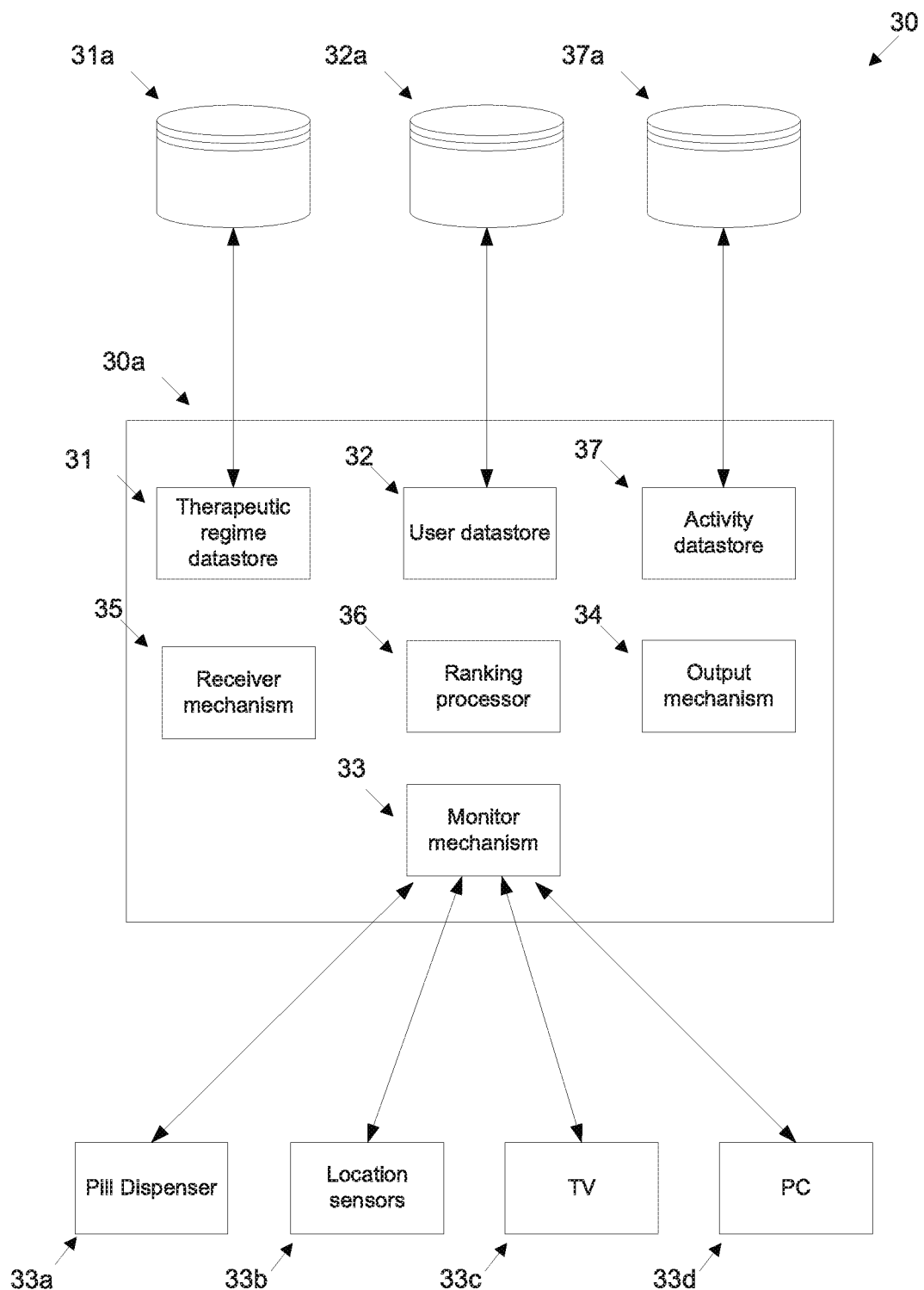
FIG. 8 schematically shows a system for messaging a user according to one or more embodiments.

FIG. 8 schematically shows a system 30 for messaging a user according to a fourth embodiment of the invention. In some embodiments the system could be used by a first user with a long term health condition, with the first user having a therapeutic regime comprising a number of therapeutic activities that the user should perform to adhere to the therapeutic regime.

The system 30 comprises a device 30a and a number of remote devices, including a remote therapeutic regime datastore 31a, a remote user datastore 32a, a remote activity database 37a, and a number of remote monitor mechanisms 33a, 33b, 33c and 33d. The device 30a comprises a therapeutic regime datastore 31, a user datastore 32, a monitor mechanism 33, an output mechanism 34, a receiver mechanism 35, a ranking processor 36, and a non-therapeutic activity datastore 37.

The device 30a is in communication with the remote reminder database 31a, the remote user datastore 32a, the remote activity database 37a, and the remote monitor mechanisms 33a, 33b, 33c and 33d via suitable interfaces. For example, the device 30a could be connected to the remote therapeutic regime datastore 31a and the remote user datastore 32a via a network, such as the internet. The device 30a could be connected to the remote monitor mechanisms 33a, 33b, 33c and 33d via a short range wireless connection, such as Bluetooth. It will, however, be appreciated that other embodiments could use other ways of connecting the remote devices to the device 30a.

In some embodiments, the device 30a is a portable device (e.g. a smart phone) carried by the user. In other embodiments, the device 30a could be a standalone device that is not portable. In other embodiments, the device 30a could be integrated into the functionality of a general purpose device.

In some embodiments, the remote monitor mechanisms are a pill dispenser 33a, location sensors 33b, a TV 33c and a personal computer (PC) 33d.

In some embodiments, the pill dispenser 33a is near field communication (NFC) enabled and can detect if the user is near the pill dispenser 33a, e.g. within a range of 1 m. In some embodiments, the user wears a suitable NFC device (e.g. a suitable bracelet), which is used by the pill dispenser 33a to detect if the user is within range. In other embodiments, the pill dispenser 33a could detect whether the user is within range by other means.

The pill dispenser 33a can also, in some embodiments, detect if a pill has been dispensed, and only dispense pills at the correct time. In some embodiments, the pill dispenser 33a can provide information on whether the user is near the pill dispenser 33a and whether a pill has been dispensed to the monitor mechanism 33. It will be assumed in the discussion below, for ease of explanation, that the pill dispenser 33a is in the user's kitchen.

In addition, in some embodiments, the pill dispenser 33a can also provide audible and visual alerts, as well as display messages.

In some embodiments, the location sensors 33b are spaced apart in the user's house and can detect where in the house the user is, providing this information to the monitor mechanism 33.

In some embodiments, the TV 33c and the personal computer (PC) 33d can detect what actions the user is performing on them (e.g. whether a favored TV show is being watched on the TV 33c or whether the internet browser of the PC 33d is being used) and can provide this information to the monitor mechanism 33. It will be assumed in the discussion below, for ease of explanation, that the TV 33c and PC 33d are in the user's living room, where it is assumed that the user spends most of him time while at home.

In some embodiments, the output mechanism 34 is capable of providing an audible, vibrating and visual message on the device 30*a*. The output mechanism 34 is also capable of instructing the pill dispenser 33*a* to provide an audible and visual message. The output mechanism 34 can also interface with the TV 33*c* to enable the TV 23*c* to display a visual message.

An example operation of such an embodiment will now be described. In this example, it will be assumed that the therapeutic regime of the first user consists of a medication regime which requires the user to take a pill twice a day, with the intervals as spaced apart and as regular as possible. It will also be assumed the first user in some embodiments is patient who is generally sedentary, spending much of his time watching television or using the internet.

The system 30 obtains therapeutic activity information about a medication regime, the therapeutic activity information including a set of time windows for taking the medication. In some embodiments, this is done by the device 30*a* querying the remote therapeutic activity database 31*a* to obtain therapeutic activity information associated with the medication regime of the patient.

The information in the therapeutic regime database 31*a* could be obtained in a variety of different ways. For example it could be obtained by a health care professional uploading a care plan that includes data such as medication, exercise regime, and diet plan that the patient needs to adhere to. The therapeutic activity information could contain information associated with all aspects of this care plan. In other embodiments, a health care professional could scan a bar code relating to a medication (or enter a suitable reference number), which would load information on the medication including the schedule for taking it. In other embodiments, the details could be obtained by the remote reminder database 31*a* in other ways, for example by manual input.

In some embodiments the therapeutic activity information includes time windows for which the medication should be taken, as the task of taking the pill must be taken twice a day.

The system 30 then obtains information on a set of user activities used to monitor the user and stores this as non-therapeutic activity information. In some embodiments, this is done by the device 30*a* querying the remote activity database 37*a* to obtain details of which activities are the most important to efficacy of messages associated with the therapeutic activities in the therapeutic activity information. The non-therapeutic activity information could also take into account the capabilities of the system 30, e.g. relating to which activities the system 30 is capable of monitoring.

In some embodiments, the monitor mechanism 33 is connected to remote monitor mechanisms that include the NFC enabled pill dispenser 33*a*, location sensors 33*b*, the TV 33*c* and the personal computer (PC) 33*d*, which are relevant to the therapeutic activity (taking a pill) in some embodiments. Hence, the non-therapeutic activity information contains the activities associated with these remote monitors, along with whether these non-therapeutic activities have a weighted positive or negative likely effect on the efficacy impact of a message associated with the therapeutic activity.

In some embodiments, the monitor mechanism 33 is further able to determine if the user is making a telephone call, and this activity is included in the activity information.

The user datastore 32 is arranged to store information on a plurality of second users, and is in communication with a remote user datastore 32*a* that contains details of other users. In some embodiments, the remote user datastore 32*a* is associated with a web portal (not shown) via with the details of the other users are obtained. In other embodiment, the remote user datastore 32*a* could contain information about other users obtained via other means (e.g. via healthcare professionals).

Once the system 30 has obtained the information on a plurality of second users, the non-therapeutic activity information and the therapeutic activity information, the system 30 can begin monitoring the user. In some embodiments, the therapeutic activity information included in the therapeutic activity information is associated with time windows for performing the therapeutic activity.

In some embodiments, the time windows could be included in the therapeutic activity information and provided to the system 30, or could be determined by the system 30 from information in the taking into account known behavior patterns of the user. In other embodiments, the time windows could be user defined or a combination of any of the above.

The monitor mechanism 33 monitors each of the non-therapeutic activities included in the non-therapeutic activity information. In some embodiments, the monitor mechanism 33 receives data from the remote monitor mechanisms 33*a*, 33*b*, 33*c* and 33*d* as well data on other non-therapeutic activities such as whether the user making a telephone call. The monitor mechanism 33 assigns an activity score to the non-therapeutic activities being monitored, depending on whether the non-therapeutic activities are being performed or not. As discussed in more detail below, the activity scores are weighted in accordance with their likely effect of a message on the likelihood of the first user performing the therapeutic activity.

The system 30 then calculates a patient convenience index by summing the activity scores, and calculates a current threshold. The ranking processor 36 determines whether the patient convenience index is above the threshold.

In some embodiments, as discussed, the TV 33*c* can monitor what is being displayed on it and provide this information to the monitor mechanism 33. In some embodiments, the TV 33*c* can monitor whether the user is watching a pay per view (ppv) film, watching a preferred TV show, or watching other TV (i.e. not a ppv film or preferred show).

In some embodiments, it is considered likely that the user watching TV will have a negative impact on the likelihood of the first user taking the pill, with watching a ppv film (where it is assumed that the user, having paid for the content, is particularly engrossed) having the most negative impact. Hence, the weights of the activity scores for "watching TV" and "watching a ppv film" could be different.

In some embodiments, as discussed, the PC 33*s* can monitor what is being used on the PC, and provide this information to the monitor mechanism 33. In some embodiments, it is considered likely that the user using the internet will have a negative impact on the likelihood of the first user taking the pill.

The location sensors 33*b* can detect that the user is moving around the house (e.g. by detecting movement from one room to another within a time period). In some embodiments, it is considered likely that the user moving around will have a negative impact on the likelihood of the first user taking the pill. This is because the user in some embodiments is generally sedentary, and thus movement around the house is likely to have specific purpose (e.g. going to the bathroom).

The location sensors 33*b* can detect that the user is in their kitchen. As the pill dispenser 33*a* is in the user's kitchen, it is considered likely that the user being in the kitchen will have a strong positive impact on the likelihood of the first user taking the pill.

The NFC enabled pill dispenser 33a can detect that the user is proximate it. Being proximate the pill dispenser 33a is to have a very strong positive impact on the likelihood of the first user taking the pill.

The monitor mechanism 33 can detect that the user is making a phone call. It is considered that making a call has a strong negative impact on the likelihood of the first user taking the pill.

The patient convenience index is the sum of the weighted activity scores in some embodiments.

$$PCI = \sum_{activities} weight \times score$$

Four states of the user are considered as states 1, 2, 3 and 4 in Table 2.

TABLE 2

| Activity | Weights | Score in State 1 | Score in State 2 | Score in State 3 | Score in State 4 |
|---|---|---|---|---|---|
| Watching a ppv film | −3 | −3 | 0 | 0 | 0 |
| Watching a preferred TV show | −2 | 0 | −2 | 0 | 0 |
| Watching other TV | −1 | 0 | 0 | −1 | 0 |
| Using the Internet | −1 | −1 | 0 | 0 | 0 |
| Moving around the house | −1 | 0 | −1 | 0 | 0 |
| In kitchen | +2 | 0 | +2 | +2 | +2 |
| Near Pill dispenser | +4 | 0 | 0 | +4 | +4 |
| Making a telephone call | −10 | 0 | 0 | 0 | −10 |
| User convenience index | | −4 | −1 | +5 | −4 |

In state 1, the user is watching a ppv film and using the internet, while sitting down. The user is therefore not likely to want to be distracted by a message to take a pill. Hence, the patient convenience index is low (−4), indicating that a message of support to take the pill at this time is unlikely to be effective.

In state 2, the user the user is watching a preferred TV show, while moving around the house and in the kitchen. It can be inferred that because a preferred TV show is being played on TV and that the user has moved to the kitchen that the user is just getting something (e.g. a drink) before going to the preferred TV show. Hence, the patient convenience index, while higher than state 1, is low (−1), indicating that a message of support to take the pill at this time is unlikely to be effective.

In state 3, the user is watching another other (non-preferred) TV show, while in the kitchen and near the pill dispenser 33a and not moving around. It can be inferred that because the user has been in the kitchen for some time (as not moving) and that a non-preferred TV show is being played on TV that the user is in the kitchen to make or eat food. The user is also physically near the pill dispenser 33a (e.g. within 1 m). The user is therefore very likely to be susceptible to a reminder in this state, and hence the patient convenience index is high (+5) indicating that a message of support to take the pill at this time is likely to be effective.

In state 4, the user is in the kitchen and near the pill dispenser 33a and not moving around. The use is also taking a phone call. While being in the kitchen, being near the pill dispenser 33a, and not moving around factors have a strong positive effect on the efficacy of the reminder to take the pill, the fact that the user is making a telephone call has a strong negative effect of the efficacy of the reminder. Hence, the patient convenience index is low (−4) indicating that a reminder a message of support to take the pill at this time is unlikely to be effective.

After ranking the messages received from second users (in any of the ways described above), reminder processor 36 determines whether the user convenience index is greater than or equal to the threshold. If so, then the output mechanism 34 will output one or more of the messages to the first user in consideration of the ranking.

Before outputting the message, the system 30 selects a message format. As discussed, in some embodiments, the output mechanism 34 is capable of providing an audible, vibrating and visual message, and the format of the reminder (e.g. purely audible, visible, or combination of audible, visual and vibrating) can vary. For example, the output format can vary according to ranking of the second user who sent the message and/or according to the message content.

In some embodiments, the user is provided with messages alerts related to their therapeutic regime at times that are considered to be appropriate for adhering to the therapeutic regime. This is done by delivering the messages when the user is carryout out (or not carrying out) certain non-therapeutic activities that are considered to have a positive or negative effect on the likelihood of the therapeutic activity being performed. Hence, such embodiments provide important benefits in ensuring that the user helps maintains their therapeutic regime.

Embodiments of the invention are suitable for messages relation to any part of a therapeutic regime, e.g. medication, exercise or any other task or activity recommended as part of the regime.

As a further example, consider an employee who is a bit overworked and his doctor has prescribed to take some moments of relaxation throughout the day. In this case the therapeutic regime comprises a treatment plan that simply includes the need to relax. Many individuals in such a situation may tend to forget about such a treatment plan in the flow of the normal workday. Embodiments of the invention (such as what is shown in FIG. 4) can help trigger the employee to relax at opportune moments. Such embodiments can ensure that his daily schedule allows for relaxation and trigger him to go for a walk or take a moment for meditation depending on his schedule and current activities.

For example, the employee could wear an activity sensor which measures his physical activity, with this activity sensor acting as a remote monitor mechanism in communication with a monitor mechanism in his tablet device. His tablet device could act as a central device in the system, and could store his calendar with his work appointments. The monitor mechanism in his tablet device could query his calendar to see when he is in a meeting (and therefore should not be bothered with messages from second users regarding relaxation). He could also wear a bracelet that measures his arousal levels, with this bracelet acting as a remote monitor mechanism in communication with a monitor mechanism in his tablet device.

In this case, a user convenience index could be calculated based on his calendar. Moments where there are no meetings could be considered convenient (e.g. +1) and moments that there are meetings are inconvenient (e.g. −1). The actual moment of finalizing the meeting can be measured based on a peak in physical activity from getting up from the chair and walking away from the meeting room to the desk (using the activity sensor). This could create a peak in the user convenience index (e.g. +4) since this is an opportune moment to trigger him for a relaxation moment (e.g., a message suggesting that he go for a walk or do a breathing exercise)

after the meeting and right before he is starting a new activity (not a meeting but potentially some task behind his desk).

When the activity stops and he sits down behind his desk again the user convenience index drops to +1 again, when a new meeting starts it drops to −1.

The longer the employee has not taken a moment to relax, a "missed therapeutic activity cost" (i.e. the negative consequence of not performing the therapeutic activity) could be set to rise. Also based on the measured arousal, the missed therapeutic activity cost could rise when arousal levels are high for too long (due to stressful activities). In this example the missed therapeutic activity cost may vary with his stress levels, being higher when he is stressful for some time, and being lower when is in a relaxed state for some time (so regardless of predetermined windows).

In a fifth embodiment of the invention, a patient (i.e. the first user) consents to sharing aspects of care plan (i.e. a therapeutic regime) with third parties (i.e. second users). The care plan may be stored as therapeutic activity information as a flag or entry associated with a database record for the patient/care plan, and be subject to privacy controls which may be selected by the patient or their carer.

Third parties (i.e. second users) can sign up through web portal to receive updates for patient. Third parties may be invited based on the social media association with the first user, based on their e-mail record, based on their mobile phone call records, based on influence factors. For example those people who have had a similar condition and who live within a 10 mile radius of the patent, may be invited to join. On joining through the portal their login details will be associated with those of the first user, and certain permissions granted to view the patients medication adherence data in line the privacy settings selected by the first user or their carer. Third parties then receive copy of aspects of care plan.

In some embodiments, medication adherence events are identified by monitoring the first user and posted together with regular updates on medication adherence. In this context, a medication adherence event can be any event which is associated with the medication plan—an event can be positive (where the patient has complied with the plan) or negative (where there has been non-compliance). Examples include taking medication prescribed, not collecting a prescription on time, taking too much medication, missing a pill etc.

In some embodiments, the monitoring mechanism (e.g. diagnostic devices) which may be used to detect compliance includes such devices as (i) instrumented pill box, (ii) eMoney purchase transactions for collecting subscriptions, (iii) instrumented pills, (iv) patient entered data etc.

The likely influence between third parties and the first user are determined. In some embodiments, a number of different methods may be used to determine this including:

1) Past usefulness: Friends and family messages could be correlated based on past usefulness (e.g. determined by how long patient spends viewing messages, a direct rank by the first user or resulted actions by the patient). Influence rank depends on strength on past usefulness. This could also be contextualized, e.g. different messages are useful for different things (pill taking, diet tips etc.)

2) Interpersonal Reactivity Index: Factors which determine empathy (which can be significant determinant of influence) based on Interpersonal Reactivity Index (and others). The questions of index to components may be assessed through electronic interactions (web forums etc.), such as:

i) Personal relationship with patient (same surname indicates family member etc.)
ii) Frequency of contact
iii) Relationship on social networks
iv) Similarity of conditions
v) Discussion of similar problems/issues or have/have had a similar care plan (can be used to determine the "Go-to" person(s)

3) Crowd-sourced voting: Yes/No voting by all users on influence of messages to the first user.

The outcome from each method may be ranked according to likely relevance using fixed criteria, or alternatively dynamically ranked according to the contextual influence between a user and a patient in a given situation.

The influence between each user and the first user is assessed—either statically, or dynamically, and ranked. The ranking is then associated with each second user. Then, third parties (i.e. second users) contribute messages of support to the first user.

Messages are entered by users giving support or advice to the patient. In some embodiments, if a second user who is ranked highly is not immediately available or has left no message, then they can be prompted by various means such as (i) text message, (ii) social media message, (iii) message to associate of the second user etc.

In some embodiments, if the highly ranked second user remains unavailable, then a flag can be set in the message scheduler (e.g. part of the output mechanism) to loop back to the step of prompting the highly ranked second user within a specific time window to try and maximize the chances of the second user sending a message.

In some embodiments, the web profile of the second user can be utilized such that their online history is used to predict their next online period, and—if this is within the time limits of a useful message posting—then a flag is set in the message schedule to prompt the highly ranked second user within a specific time window to try and maximize the chances of the second user sending a message.

In some embodiments, messages from second users are ranked according to (i) overall influence and (ii) contextual influence. Messages are ranked according to likely influence based on:
  i. Influence of user creating message and first user
  ii. Contextual influence between the second user and the first user's current situation
  iii. Content of message and the first user's current situation The time of delivery of messages to the first user is then scheduled. In some embodiments, the most appropriate time to communicate message to the first user computed (e.g., immediately after the event, immediately prior to the next possible occasion for the event to occur, before going to bed, during a moment of reflection) which may depend on the message contents and adherence event.

In some embodiments, the scheduler may function, for example, by modeling the desirability of delivering messages relating to specific adherence events at certain times, possibly by also considering the message contents.

In some embodiments, a looping structure can be incorporated to collect more messages, such that a loop back to the step of collecting messages from the second users during the time window when messages can be delivered is initiated under certain conditions (e.g., more messages are required for the message scheduler)

In some embodiments, the elected messages are communicated through the communication device which—at the time the message is communicated—has most contextual influence with the first user. For example, all communication devices available to first user can be ranked according to the capability of the device to most influentially communicate the message to the first user. For example, the communication devices could be ranked as follows:
  i. Identify all networked communication devices
  ii. Derive activity of first user
  iii. Calculate which communications device is most influence for first user's context
  iv. Communicate message
  c. Map message to communication device
  i. The message with most influence can be mapped to the most influential communications device, and so forth. However variations in this mapping may be implemented.

In some embodiments, messages from high ranked second users may be sent to two or more communications devices, or be highlighted by the use of a larger font etc.

In some embodiments, an iterative feedback system may be incorporated so as to reward users who make acted on comments with a higher influence ranking, and reduce the ranking of those who do not.

To help explain the operation of the embodiments of the invention further, another example situation will be discussed.

In this example, the first user has Congestive heart failure (CHF), which is an inability of the heart to provide sufficient pump action to distribute blood flow to meet the needs of the body. CHF can cause a number of symptoms including shortness of breath, leg swelling, and exercise intolerance. Treatment for CHF commonly consists of lifestyle measures such as smoking cessation, light exercise including breathing protocols, decreased salt intake and other dietary changes, and medications. Sometimes it is treated with implanted devices (pacemakers or ventricular assist devices) and occasionally a heart transplant.

As such, CHF represents an example of a long term health condition that requires a therapeutic regime comprising a number of therapeutic activities. Non-adherence to the therapeutic regime is likely to lead to health problems.

For CHF the critical medications are typically beta blockers and diuretics. If these are being taken correctly (i.e. according to the user's therapeutic regime), then the user has the best chance of remaining stable with CHF. However, not taking the beta blockers can lead to arrhythmias, and not taking the diuretics can lead to lung edema. Both of these conditions can be life threatening and may require hospitalization. They are generally called "CHF decompensation".

In this example, the first user will be referred to as Patient A. Patient A has CHF and is required to take beta blockers and diuretics. The taking of beta blockers and diuretics are each separate therapeutic activities in Patient A's therapeutic regime. In this example, the beta blockers proscribed to Patient A are new.

Patient A agrees to share their care plan with Users W, X, Y. Users W, X, Y, along with Patient A, use a web portal to share information with other others. In addition to Users W, X, Y, a large number of other users use the web portal and these other users also receive the care plan of Patient A.

User W has had the same condition, i.e. CHF, as Patient A. User W's therapeutic regime comprises taking the same diuretics as Patient A, but a different type of beta blocker.

User X has specific knowledge of the new beta blockers taken by Patient A but not experienced by User W.

User Y lives in the same village as Patient A.

Patient A receives a care plan from their consultant and agrees to share defined aspects of this plan with other users that use the web portal. Hence, the care plan including details of the therapeutic regime is stored on the web portal. Users W, X and Y can receive extracts from the plan via the web portal.

The influence between Patient A and Users W, X and Y is assessed using a variety of different techniques.

User W is rated as having the highest overall influence due to having suffered a similar condition previously and having been voted by other users as having previously produced supporting messages of a high level of influence with the patient.

User X is selected as having the greatest influence for the new medication which has not been experienced by User W and also scores highly based in the interpersonal reactivity index based on data mined from the web.

User Y is rated as having the great location based influence based on data mined from the web, and has also been voted by other users as having previously produced supporting messages of a high level of influence with the patient.

Scenario 1

In this scenario, the system used by Patient A (i.e. the first user) has an instrumented pill taking as part of the monitoring mechanism. The instrumented pill taking system indicates that Patient A has just taken the first dose of the new medicine which creates an adherence event.

User X, as the person with greatest contextual influence for the new medicine is prompted to leave a message and all other users are free to also leave message.

User X is initially unavailable, but eventually leaves a message 2 hours after the adherence event The message of User X is ranked highest due to the contextual influence, with User W the next highest. There are also 10 other messages of support from other users.

In this scenario, the communication means available to Patient A are mobile device text message, mobile device e-mail message, mobile device on-screen portal message, television message and pill-box on screen message.

The communication means are ranked according to their context with the patient event. The ranking is (1) pill-box screen message, (2) television message, (3) mobile device text message.

The message from User X is displayed on the pill-box just before the patient goes to bed, which has been scheduled as being the mostly influential time on Patient A, and all 12 (10+2) messages are scheduled and displayed on the television during an advertising break, or break between programs, which is being viewed by Patient A.

Scenario 2

In this scenario, eMoney transaction data indicates that Patient A is late collecting their pill prescription from the local pharmacy, which creates an adherence event.

User Y, as the person with greatest contextual influence for location is prompted to leave a message and all other users are free to also leave message. The message of User Y is ranked highest due to the contextual influence, with User W the next highest. There are also 5 other messages of support.

In this scenario, the communication means available to Patient A are mobile device text message, mobile device e-mail message, mobile device audio message, television message and pill-box on screen message.

The communication means are ranked according to their context with the patient event. The ranking is (1) mobile device text message, (2) mobile device on-screen portal message, (3) television message. Mobile devices means of communication are ranked highest as the patient is not currently watching television, but mobile phone location data indicates they are moving within their home.

The message from User Y is sent as a text message, and all 12 (10+2) messages are loaded as an on-screen portal message with ranking such that Y and W are most visible (larger font, list first etc.)

Another embodiment of the invention will now be described. In some embodiments, users are categorized into one of a predetermined number of psychological profiles. The information on the psychological profile can be stored in the therapeutic regime datastore, or in another storage unit of the system.

As a result, the second users can be ranked according to the psychological profile of the first user to rank the second users. In other words, those second users with compatible profiles (which may be the same profile type or a different profile type depending on the profile type of the first user) can be ranked higher.

In some embodiments, the ranking processor 16 is arranged to use the communications method used by the second users to send messages to the first user in the ranking. This can be used along with the profile of the first user to determine the ranking of the second users.

As a result, the ranking of the second users can be determined based on the delivery modes that second user has available and the match these have with the psychological profile of the first user (e.g. more personal delivery vs. less personal delivery) as well as and the relationship he has with the patient and the communication style he has.

It will be appreciated that the psychological profile of the first user could be used to rank the second users in a number of different ways.

In some embodiments, the user datastore can be arranged to store information on the psychological profiles of the second users. In some embodiments, the ranking processor can use the psychological profiles of the second users to determine the ranking. For example, ranking processor could use the psychological profile of the first user and the psychological profiles of the second users to determine the ranking.

In some embodiments, the ranking processor could use the psychological profile of the first user, the psychological profiles of the second users, and the communication method used by (or available to) the second users to determine the ranking.

Hence, as described above, embodiments of the invention provide an improved system and method for messaging a user. Such a system provides messages (e.g. messages of support) to the first user from second users. The ranking of the messages from the second users and the output of the messages in consideration of this ranking ensures that the most important or most relevant messages are given the appropriate attention by the first user. This avoids the technical issue of the user having a great many messages to sift through to get to the important messages. It also helps ensure that important messages are not missed by the user.

In a number of the examples above, the first user has a long term health condition. It will, of course, be appreciated that embodiments of the invention are equally applicable to any condition, be it a long term condition or a short term one.

It will be appreciated that the hardware used by embodiments of the invention can take a number of different forms. For example, all the components of the system could be provided by a single device (e.g. the example of FIG. 2 in conjunction with a web portal), or different components of the system could be provided on separate devices. Examples of such arrangements are the system of FIG. 4, in which a number of the components of the respective systems are provided on a device, whereas other components are provided on remote devices (with "remote" in this context meaning not part of the device, but communicable with the device). More generally, it will be appreciated that embodiments of the invention can provide a system that comprises one device or several devices in communication.

It will be appreciated that the term "comprising" does not exclude other elements or steps and that the indefinite article "a" or "an" does not exclude a plurality. A single processor may fulfill the functions of several items recited in the claims. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

Additional example embodiments are provided with reference to the following enumerated embodiments:

A1. A method comprising: storing therapeutic activity information including information on therapeutic activities forming part of a therapeutic regime of a first user, the therapeutic regime of the first user relating to a health condition of the first user; storing information on a plurality of second users; monitoring the first user to determine if the first user performs a therapeutic activity for which therapeutic activity information is stored in the therapeutic regime datastore and to produce an adherence result for that therapeutic activity based on the determination; outputting information to the second users regarding the adherence result; receiving messages from the second users to the first user relating to the adherence result; assigning a ranking score to each of the second users, with the ranking score relating to the likely influence between a said second user and the first user; and outputting one or more messages from the second users to the first user in consideration of the ranking scores.

A2. The method of embodiment A1, wherein the ranking score relates to the likely influence of the said second user on the adherence of the first user to the therapeutic regime.

A3. The method of any of embodiments A1-A2, further comprising: determining if the therapeutic activity is subsequently performed by the first user following the output of a said message from one of the second users; storing information on which second users' messages are effective in causing the therapeutic activity to be performed following the output of the messages; and assigning higher ranking scores to those second users whose messages are effective in causing the therapeutic activity to be performed following the output of the messages.

A4. The method of any of embodiments A1-A3, further comprising: storing information on the relationships between the plurality of second users and the first user; and assigning higher ranking scores to those second users with closer relationships to the first user.

A5. The method of any of embodiments A1-A4, further comprising: storing information on location proximity between the plurality of second users and the first user; and assigning higher ranking scores to those second users who are near to the first user.

A6. The method of any of embodiments A1-A5, further comprising: storing information on the frequency of contact between the each of the second users and the first user; and assigning higher ranking scores to those second users with more frequent contact with the first user.

A7. The method of any of embodiments A1-A6, further comprising: storing information on health conditions of the second users; and assigning higher ranking scores to those second users with similar health conditions to the health condition of the first user.

A8. The method of any of embodiments A1-A7, further comprising: storing information on therapeutic activities carried out by the second users; and storing higher ranking scores to those second users who carry out similar therapeutic activities to the therapeutic activity of the first user.

A9. The method of any of embodiments A1-A8, further comprising: determining how long the first user spends viewing messages from each of the second users; storing this information in the user datastore; and assigning higher ranking scores to those second users whose messages are viewed for longer by the first user.

A10. The method of any of embodiments A1-A9, further comprising: receiving an input from the user indicating how useful the first user found each message from the second users in aiding adherence to the therapeutic regime, wherein the input is used in the determining of the ranking scores.

A11. The method of any of embodiments A1-A10, further comprising: assigning different ranking scores to the second users depending on the nature of the adherence result.

A12. The method of any of embodiments A1-A11, further comprising: assigning different ranking scores to the second users depending on the content of the messages sent by the second users.

A13. The method of any of embodiments A1-A12, further comprising: comparing the ranking scores of those second users for which messages are received with a stored threshold, and wherein if the ranking scores of those second users for which messages are received are below the stored threshold, outputting a message prompt to second users whose ranking scores are above the stored threshold.

A14. The method of any of embodiments A1-A13, further comprising: following the output of the message prompt, if no messages are received from those second users whose ranking scores are above the stored threshold within a predetermined time window, outputting a further message prompt to those second users whose ranking scores are above the stored threshold.

A15. The method of any of embodiments A1-A14, further comprising: storing non-therapeutic activity information comprising information on non-therapeutic activities that are considered to have an effect on the impact of the message; monitoring the user to determine if the user is performing one or more non-therapeutic activities for which non-therapeutic activity information is stored in the activity datastore; producing a monitoring result based on the determination; determining when to send the first user the one or more messages from the second users based on the monitoring result; comparing the monitoring result to a stored parameter; timing the output the one or more messages from the second users to the first user on the basis of the comparison of the monitoring result and the stored parameter;

A16. The method of embodiment A15, wherein the impact of the message relates to the likelihood of the first user performing the therapeutic activity.

A17. The method of any of embodiments A15-A16, wherein the stored parameter is a threshold, further comprising: outputting the one or more messages from the second users to the first user when the monitoring result meets or exceeds the threshold.

A18. The method of any of embodiments A15-A17, further comprising: monitoring each activity in the activity information; and assigning an activity score based on whether that activity is being performed;

A19. The method of any of embodiments A15-A18, wherein the monitoring result is the sum of the activity scores.

A20. The method of any of embodiments A15-A19, further comprising: assigning different weight values to different activities scores.

A21. The method of any of embodiments A1-A21, wherein the output mechanism comprises a number of devices capable of outputting the messages to the first user, further comprising: determining which of the said devices to use to output each message to the user based on the therapeutic activity to which each message relates.

A22. The method of any of embodiments A1-A22, further comprising: storing information relating to a psychological profile of the first user; and using the psychological profile of the first user to rank the second users.

B1. A method comprising: obtaining a first set of candidate users for messaging with a first user in connection with occurrence of a first trigger associated with the first user, the first set of candidate users comprising a second user and a third user; monitoring, via one or more sensors, the first user for occurrence of the first trigger; determining a first occurrence of the first trigger based on the monitoring; and initiating messaging between the first user and the second user.

B2. The method of embodiment B1, wherein messaging is initiated between the first user and the second user based on the second user having a higher priority than the third user of the first set of candidate users.

B3. The method of any of embodiments B1-B2, further comprising: initiating messaging between the first user and the third user based on (i) the third user having a higher priority than one or more other users of the first set of candidate users and (ii) the second user being determined to be unavailable.

B4. The method of any of embodiments B1-B3, further comprising: determining whether an initiation threshold for initiation of messaging between the first user and unavailable users has been reached in connection with the first occurrence of the first trigger; and transmitting a prior message of at least one user of the first set of candidate users to the first user in connection with the first occurrence of the first trigger based on the determination that the initiation threshold has been reached.

B5. The method of embodiment B4, wherein the threshold comprises (i) initiation of messaging between the first user and a threshold number of unavailable users in connection with the first occurrence of the first trigger or (ii) a threshold amount of time passing since initiation of messaging between the first user and the second user without obtaining a message from one or more users of the first set of candidate users in connection with the first occurrence of the first trigger; and B6. The method of any of embodiments B1-B5, further comprising: performing a query for one or more prior messages of one or more users of the first set of candidate users that (i) was submitted in connection with a prior occurrence of the first trigger and (ii) has not been received by the first user; and obtaining the prior message based on the query for the one or more prior messages for transmission to the first user in connection with the first occurrence of the first trigger.

B7. The method of any of embodiments B1-B6, wherein monitoring the first user comprises monitoring adherence of the first user via the one or more sensors.

B8. The method of any of embodiments B1-B7, wherein monitoring the first user comprises monitoring the adherence of the first user via the one or more sensors, and wherein initiating messaging between the first user and the second user is based on (i) the adherence data indicating the first occurrence of the first trigger and (ii) the second user having a higher priority than the third user of the first set of candidate users.

B9. The method of any of embodiments B1-B8, wherein monitoring the first user comprises monitoring the location data associated with the first user via the one or more sensors, and wherein initiating messaging between the first user and the second user is based on (i) the location data indicating the first occurrence of the first trigger and (ii) the second user having a higher priority than the third user of the first set of candidate users.

B10. The method of any of embodiments B1-B9, further comprising: obtaining training user datasets representing a plurality of users, each user dataset of the training user datasets comprising data representing one or more attributes of a user of the plurality of users; using the training user datasets to train a prediction model to predict a set of candidate users for messaging with a user in connection with occurrence of a trigger associated with the user; updating one or more configurations of the prediction model based on training response data comprising data related to responses of the user to messaging with one or more users of the set of candidate users; and subsequent to the updating of the prediction model, obtaining, via the prediction model, the first set of candidate users for messaging with the first user in connection with occurrence of the first trigger associated with the first user.

B11. The method of embodiment B10, further comprising: obtaining response data related to the first user the response data comprising data related to responses of the first user to messaging with one or more users of the first set of candidate users; and updating one or more configurations of the prediction model based on the response data related to the first user to the prediction model.

B12. The method of embodiment B11, wherein the prediction model comprises a neural network or other machine learning model.

C1. One or more tangible, non-transitory, machine-readable media storing instructions that, when executed by one or more processors, effectuation operations comprising those of any of embodiments A1-A22 and B1-B12.

C2. A system comprising: one or more processors; and memory storing computer program instructions that, when executed by the one or more processors, cause the one or more processors to effectuate operations comprising those of any of embodiments A1-A22 and B1-B12.

What is claimed is:

1. A system for facilitating trigger-associated user messaging, the system comprising:
a computer system that comprises one or more processors executing computer program instructions that, when executed, cause the computer system to:
obtain training user datasets representing a plurality of users, each user dataset of the training user datasets comprising data representing one or more attributes of a user of the plurality of users;
provide the training user datasets to a neural network to train the neural network in a first stage to predict a list of candidate users for messaging with a user in connection with occurrence of a trigger associated with the user;
provide training response data to the neural network as reference feedback to train the neural network in a second stage, the neural network updating one or more layers of the neural network based on the training response data, the training response data comprising data related to responses of the user to messaging with one or more users of the list of candidate users;
subsequent to the training of the neural network, obtain, from the neural network, a first list of candidate users for messaging with a first user in connection with occurrence of a first trigger associated with the first user, the first list of candidate users comprising a second user and a third user;
monitor, via one or more sensors, the first user for occurrence of the first trigger;
access, based on the monitoring indicating a first occurrence of the first trigger, the first list of candidate users to initiate messaging between the first user and one or more users of the first list of candidate users;
initiate messaging between the first user and the second user based on the second user having a higher priority than the third user of the first list of candidate users;
initiate messaging between the first user and the third user based on (i) the third user having a higher priority than one or more other users of the first list of candidate users and (ii) the second user being determined to be unavailable;
determine whether an initiation threshold for initiation of messaging between the first user and unavailable users has been reached in connection with the first occurrence of the first trigger, the threshold comprising (i) initiation of messaging between the first user and a threshold number of unavailable users in connection with the first occurrence of the first trigger or (ii) a threshold amount of time passing since initiation of messaging between the first user and the second user without obtaining a message from one or more users of the first list of candidate users in connection with the first occurrence of the first trigger; and transmit a prior message of at least one user of the first list of candidate users to the first user in connection with the first occurrence of the first trigger based on the determination that the initiation threshold has been reached.

2. The system of claim 1, wherein the computer system is caused to:
obtain response data related to the first user, the response data comprising data related to responses of the first user to messaging with one or more users of the first list of candidate users; and
provide the response data related to the first user to the neural network as reference feedback for the neural network's prediction of the first list of candidate users, the neural network updating one or more layers of the neural network based on the response data.

3. The system of claim 1, wherein the computer system is caused to:
perform a query for one or more prior messages of one or more users of the first list of candidate users that (i) was submitted in connection with a prior occurrence of the first trigger and (ii) has not been received by the first user; and
obtain the prior message based on the query for the one or more prior messages for transmission to the first user in connection with the first occurrence of the first trigger.

4. The system of claim 1, wherein monitoring the first user comprises monitoring adherence data associated with the first user via the one or more sensors.

5. A method comprising:
obtaining, by one or more processors, training user datasets representing a plurality of users, each user dataset of the training user datasets comprising data representing one or more attributes of a user of the plurality of users;
using, by one or more processors, the training user datasets to train a prediction model to predict a set of candidate users for messaging with a user in connection with occurrence of a trigger associated with the user;
updating, by one or more processors, one or more configurations of the prediction model based on training response data comprising data related to responses of the user to messaging with one or more users of the set of candidate users;
subsequent to the updating of the prediction model, obtaining, by one or more processors, via the prediction model, a first set of candidate users for messaging with a first user in connection with occurrence of a first trigger associated with the first user, the first set of candidate users comprising a second user and a third user;
monitoring, by one or more processors, via one or more sensors, the first user for occurrence of the first trigger;
initiating, by one or more processors, messaging between the first user and the second user based on (i) the monitoring indicating a first occurrence of the first trigger and (ii) the second user having a higher priority than the third user of the first set of candidate users;
initiating, by one or more processors, messaging between the first user and the third user based on (i) the third user having a higher priority than one or more other users of the first set of candidate users and (ii) the second user being determined to be unavailable;
determining whether an initiation threshold for initiation of messaging between the first user and unavailable users has been reached in connection with the first occurrence of the first trigger, the threshold comprising (i) initiation of messaging between the first user and a threshold number of unavailable users in connection with the first occurrence of the first trigger or (ii) a threshold amount of time passing since initiation of messaging between the first user and the second user without obtaining a message from one or more users of the first set of candidate users in connection with the first occurrence of the first trigger; and
transmitting a prior message of at least one user of the first set of candidate users to the first user in connection with the first occurrence of the first trigger based on the determination that the initiation threshold has been reached.

6. The method of claim 5, further comprising:
obtaining response data related to the first user the response data comprising data related to responses of the first user to messaging with one or more users of the first set of candidate users; and
updating one for more configurations of the prediction model based on the response data related to the first user.

7. The method of claim 6, further comprising:
performing a query for one or more prior messages of one or more users of the first set of candidate users that (i) was submitted in connection with a prior occurrence of the first trigger and (ii) has not been received by the first user; and
obtaining the prior message based on the query for the one or more prior messages for transmission to the first user in connection with the first occurrence of the first trigger.

8. The method of claim 5, wherein monitoring the first user comprises monitoring adherence associated with the first user via the one or more sensors.

9. The method of claim 8, wherein monitoring the first user comprises monitoring the adherence associated with the first user via the one or more sensors, and
wherein initiating messaging between the first user and the second user is based on (i) the adherence data indicating the first occurrence of the first trigger and (ii) the second user having a higher priority than the third user of the first set of candidate users.

10. The method of claim 8, wherein monitoring the first user comprises monitoring the location data associated with the first user via the one or more sensors, and
wherein initiating messaging between the first user and the second user is based on (i) the location data indicating the first occurrence of the first trigger and (ii) the second user having a higher priority than the third user of the first set of candidate users.

11. The method of claim 5, wherein the prediction model comprises a neural network.

12. One or more non-transitory computer-readable media comprising one or more instructions that, when executed by one or more processors, cause operations comprising:
obtaining training user datasets representing a plurality of users, each user dataset of the training user datasets comprising data representing one or more attributes of a user of the plurality of users;
providing the training user datasets to a neural network to train the neural network in a first stage to predict a list of candidate users for messaging with a user in connection with occurrence of a trigger associated with the user;
providing training response data to the neural network as reference feedback to train the neural network in a second stage, the neural network updating one or more layers of the neural network based on the training response data, the training response data comprising data related to responses of the user to messaging with one or more users of the list of candidate users;

subsequent to the training of the neural network, obtaining, from the neural network, a first list of candidate users for messaging with a first user in connection with occurrence of a first trigger associated with the first user, the first list of candidate users comprising a second user and a third user;

monitoring, via one or more sensors, the first user for occurrence of the first trigger;

accessing, based on the monitoring indicating a first occurrence of a first trigger, the first list of candidate users to initiate messaging between the first user and one or more users of the first list of candidate users;

initiating messaging between the first user and the second user based on the second user having a higher priority than the third user of the first set of candidate users;

initiating messaging between the first user and the third user based on (i) the third user having a higher priority than one or more other users of the first list of candidate users and (ii) the second user being determined to be unavailable;

determining whether an initiation threshold for initiation of messaging between the first user and unavailable users has been reached in connection with the first occurrence of the first trigger, the threshold comprising (i) initiation of messaging between the first user and a threshold number of unavailable users in connection with the first occurrence of the first trigger or (ii) a threshold amount of time passing since initiation of messaging between the first user and the second user without obtaining a message from one or more users of the first set of candidate users in connection with the first occurrence of the first trigger; and transmitting a prior message of at least one user of the first set of candidate users to the first user in connection with the first occurrence of the first trigger based on the determination that the initiation threshold has been reached.

13. The one or more non-transitory computer-readable media of claim 12, the operations further comprising:
initiating messaging between the first user and the third user based on (i) the third user having a higher priority than one or more other users of the first set of candidate users and (ii) the second user being determined to be unavailable.

14. The one or more non-transitory computer-readable media of claim 12, the operations further comprising:
performing a query for one or more prior messages of one or more users of the first set of candidate users that (i) was submitted in connection with a prior occurrence of the first trigger and (ii) has not been received by the first user; and
obtaining the prior message based on the query for the one or more prior messages for transmission to the first user in connection with the first occurrence of the first trigger.

15. The one or more non-transitory computer-readable media of claim 12, wherein monitoring the first user comprises monitoring adherence of the first user via the one or more sensors.

16. The one or more non-transitory computer-readable media of claim 15, wherein monitoring the first user comprises monitoring the adherence of the first user via the one or more sensors, and
wherein initiating messaging between the first user and the second user is based on (i) the adherence data indicating the first occurrence of the first trigger and (ii) the second user having a higher priority than the third user of the first set of candidate users.

17. The one or more non-transitory computer-readable media of claim 15, wherein monitoring the first user comprises monitoring the location data associated with the first user via the one or more sensors, and
wherein initiating messaging between the first user and the second user is based on (i) the location data indicating the first occurrence of the first trigger and (ii) the second user having a higher priority than the third user of the first set of candidate users.

* * * * *